United States Patent
Gambini et al.

(10) Patent No.: US 6,518,068 B1
(45) Date of Patent: Feb. 11, 2003

(54) LUMINESCENCE DETECTION WORKSTATION

(75) Inventors: Michael R. Gambini, Bolton, MA (US); John C. Voyta, Sudbury, MA (US); John Atwood, deceased, late of Redding, CT (US), Susan A. Atwood-Stone, executrix; Bruce E. DeSimas, II, Danville, CA (US); Edward Lakatos, Bethel, CT (US); Jeff Levi, Trumbull, CT (US); Israel Metal, Flushing, NY (US); George Sabak, Monroe, CT (US); Yongdong Wang, Wilton, CT (US)

(73) Assignee: Tropix, Inc., Bedford, MA (US)

( * ) Notice: Subject to any disclaimer, the term of this patent is extended or adjusted under 35 U.S.C. 154(b) by 182 days.

(21) Appl. No.: 09/621,961

(22) Filed: Jul. 21, 2000

Related U.S. Application Data
(60) Provisional application No. 60/144,891, filed on Jul. 21, 1999.

(51) Int. Cl.[7] ............................................. G01N 21/64
(52) U.S. Cl. ..................... 436/50; 436/172; 422/52; 422/67; 422/82.08; 250/361 C
(58) Field of Search ..................... 422/63, 67, 82.08, 422/52; 250/361 C; 436/47, 50, 172

(56) References Cited

U.S. PATENT DOCUMENTS

| | | |
|---|---|---|
| 4,099,920 A | 7/1978 | Heiss |
| 4,366,118 A | 12/1982 | Bunce et al. |
| 4,772,453 A | 9/1988 | Lisenbee |
| 5,329,353 A | * 7/1994 | Ichimura et al. ............ 356/301 |
| 5,854,684 A | * 12/1998 | Stabile et al. ............... 356/417 |

FOREIGN PATENT DOCUMENTS

| | | |
|---|---|---|
| EP | 0 025 350 | 3/1981 |
| EP | 0640828 A1 * | 3/1995 |

* cited by examiner

Primary Examiner—Jeffrey Snay
(74) Attorney, Agent, or Firm—Piper Rudnick LLP; Steven B. Kelber

(57) ABSTRACT

A luminescence detecting apparatus and method for analyzing luminescent samples is disclosed. Luminescent samples are placed in a plurality of sample wells in a tray, and the tray is placed in a visible-light impervious chamber containing a charge coupled device camera. The samples may be injected in the wells, and the samples may be injected with buffers and reagents, by an injector. In the chamber, light from the luminescent samples pass through a collimator, a Fresnel field lens, a filter, and a camera lens, whereupon a focused image is created by the optics on the charge-coupled device (CCD) camera. The use of a Fresnel field lens, in combination with a collimator and filter, reduces crosstalk between samples below the level attainable by the prior art. Preferred embodiments of the luminescence detecting apparatus and method disclosed include central processing control of all operations, multiple wavelength filter wheel, and robot handling of samples and reagents. Preferred embodiments of processing software integrated with the invention include elements for mechanical alignment, outlier shaving, masking, manipulation of multiple integration times to expand the dynamic range, crosstalk correction, dark subtraction interpolation and drift correction, multi-component analysis applications specifically tailored for luminescence, and uniformity correction.

30 Claims, 15 Drawing Sheets

LUMINESCENCE DETECTION WORKSTATION

This application claims the benefit from Provisional Application Serial No. 60/144,891, filed Jul. 21, 1999. The entirety of that provisional application is incorporated herein by reference.

BACKGROUND OF THE INVENTION

1. Field of the Invention

This invention relates to the field of apparatus and methods for detecting and quantifying light, emissions, and more particularly, to detecting and quantifying light emitted from luminescent-based assays. Still more particularly, this invention pertains to apparatus and methods for detecting and quantifying luminescence such as bioluminescence and/or chemiluminescence from luminescent assays as an indicator of the presence or amount of a target compound. Preferred embodiments of the invention include as an imaging device a charge coupled device (CCD) camera and a computer for analyzing data collected by the imaging device. Further preferred embodiments include the capacity for use in high throughput screening (HTS) applications, and provide for robot handling of assay plates.

2. Description of the Related Art

The analysis of the luminescence of a substance, and specifically the analysis of either bioluminescence (BL) or chemiluminescence (CL), is becoming an increasingly useful method of making quantitative determinations of a variety of luminescent analytes.

Recently, methods have been introduced that utilize luminescence detection for quantitatively analyzing analytes in an immunoassay protocol. Such luminescence immunoassays (LIA) offer the potential of combining the reaction specificity of immunospecific antibodies or hybridizing nucleic acid sequences and similar specific ligands with the high sensitivity available through light detection. Traditionally, radioactive reagents have been used for such purposes, and the specificity and sensitivity of LIA reagents is generally comparable to those employing traditional radiolabelling. However, LIA is the preferred analytical method for many applications, owing to the nontoxic nature of LIA reagents and the longer shelf lives of LIA reagents relative to radioactive reagents.

Among other luminescent reagents, chemiluminescent compounds such as 1,2-dioxetanes, developed by Tropix, Inc. and other stable chemiluminescent molecules, such as xanthan esters and the like, are in commercial use. These compounds are triggered to release light through decomposition triggered by an agent, frequently an enzyme such as alkaline phosphatase, which is present only in the presence, or specific absence, of the target compound. The detection of light emission is a qualitative indication, and the amount of light emitted can be quantified as an indicator of the amount of triggering agent, and therefore target compound, present. Other well known luminescent compounds can be used as well.

Luminescent release may sometimes be enhanced by the presence of an enhancement agent that amplifies or increases the amount of light released. This can be achieved by using agents which sequester the luminescent reagents in a microenviroment which reduces suppression of light emission. Much biological work is done, perforce, in aqueous media. Water typically suppresses light emission. By providing compounds, such as water soluble polymeric onium salts (ammonium, phosphonium, sulfonium, etc.) small regions where water is excluded that may sequester the light emitting compound may be provided.

The majority of instrumentation used to monitor light emitting reactions (luminometers) use one or more photomultiplier tubes (PMTs) to detect the photons emitted. These are designed to detect light at the low light levels associated with luminescent reactions. The rate at which a PMT based microplate luminometer can measure signal from all wells of the plate is limited by the number of PMTs used. Most microplate luminometers have only one PMT so a 384 well plate requires four times longer than is required to read a 96-well plate.

The nature of biological research dictates that numerous samples be assayed concurrently, e.g., for reaction of a chemiluminescent substrate with an enzyme. This is particularly true in gene screening and drug discovery, where thousands of samples varying by concentration, composition, media, etc. must be tested. This requires that multiple samples be reacted simultaneously, and screened for luminescence. However, there is a need for high speed processing, as the chemiluminescence or bioluminescence may diminish with time. Simultaneously screening multiple samples results in improved data collection times, which subsequently permits faster data analysis, and contingent improved reliability of the analyzed data.

In order for each specific sample analyte's luminescence to be analyzed with the desired degree of accuracy, the light emission from each sample must be isolated from the samples being analyzed concurrently. In such circumstances, stray light from external light sources or adjacent samples, even when those light levels are low, can be problematic. Conventional assays, particularly those employing high throughput screening (HTS) use microplates, plastic trays provided with multiple wells, as separate reaction chambers to accommodate the many samples to be tested. Plates currently in use include 96- and 384-well plates. In response to the increasing demand for HTS speed and miniaturization, plates having 1,536 wells are being introduced. An especially difficult impediment to accurate luminescence analysis is the inadvertent detection of light in sample wells adjacent to wells with high signal intensity. This phenomenon of light measurement interference by adjacent samples is termed 'crosstalk' and can lead to assignment of erroneous values to samples in the adjacent wells if the signal in those wells is actually weak.

Some previously proposed luminometers include those described in U.S. Pat. No. 4,772,453; U.S. Pat. No. 4,366,118; and European Patent No. EP 0025350. U.S. Pat. No. 4,772,453 describes a luminometer having a fixed photodetector positioned above a platform carrying a plurality of sample cells. Each cell is positioned in turn under an aperture through which light from the sample is directed to the photodetector. U.S. Pat. No. 4,366,118 describes a luminometer in which light emitted from a linear array of samples is detected laterally instead of above the sample. Finally, EP 0025350 describes a luminometer in which light emitted through the bottom of a sample well is detected by a movable photodetector array positioned underneath the wells.

Further refinements of luminometers have been proposed in which a liquid injection system for initiating the luminescence reaction just prior to detection is employed, as disclosed in EP 0025350. Also, a temperature control mechanism has been proposed for use in a luminometer in U.S. Pat. No. 4,099,920. Control of the temperature of luminescent samples may be important, for example, when it is desired to incubate the samples at an elevated temperature.

A variety of light detection systems for HTS applications are available in the market. These include the LEADseeker™ from Amersham/Pharmacia, the ViewLux™ offered by PerkinElmer and CLIPR™ from Molecular Devices. These devices are all expensive, large dimensioned (floorbased models), exhibit only limited compatibility with robotic devices for plate preparation and loading, have a limited dynamic range, and/or use optical detection methods which do not reduce, or account for, crosstalk. The optical systems used are typically complex teleconcentric glass lens systems, which may provide a distorted view of wells at the edges of the plates, and the systems are frequently expensive, costing in excess of $200,000.00. Perhaps the most popular detection apparatus is the TopCount™, a PMT-based detection system from Packard. Although the TopCount™ device has a desirable dynamic range, it is not capable of reading 1,536 well plates, and it does not image the whole plate simultaneously.

Crosstalk from adjacent samples remains a significant obstacle to the development of improved luminescence analysis in imaging-based systems. This can be appreciated as a phenomenon of simple optics, where luminescent samples produce stray light which can interfere with the light from adjacent samples. Furthermore, the development of luminometers capable of detecting and analyzing samples with extremely low light levels are particularly vulnerable to crosstalk interference.

SUMMARY OF THE INVENTION

In order to meet the above-identified needs that are unsatisfied by the prior art, it is a principal object and purpose of the present invention to provide a luminescence detecting apparatus that will permit the analysis of luminescent samples. It is a further object of the present invention to provide a luminescence detecting apparatus capable of simultaneously analyzing a large number of luminescent samples. In a preferred embodiment of the present invention, a luminescence detecting apparatus is provided that simultaneously analyzes multiple samples held in wells, where the well plates contain as many as 1,536 wells. The present invention further includes robot handling of the multiple well trays during analysis.

It is yet another object of the present invention to provide a luminescence detecting apparatus capable of analyzing low light level luminescent samples, while minimizing crosstalk from adjacent samples, including and especially minimizing crosstalk from adjacent samples with higher light level output than the sample to be analyzed.

The apparatus of this invention employs a Fresnel lens arrangement, with a vertical collimator above the well plate, with dimensions to match the number of wells. Thus, a 1,536-well plate will employ a dark collimator above the plate with 1,536 cells in registry with the wells of the plate. Fixed above the collimator is a Fresnel lens, which refracts the light such that the view above the lens appears to be looking straight down into each well, regardless of its position on the plate, even at the edges.

Above the Fresnel lens is a CCD camera arranged so as to take the image of the entire plate at one time, viewing through a 35 mm wide angle lens, to give whole plate imaging on a rapid basis. Between the CCD and Fresnel/collimator is a filter, typically arrayed on a filter wheel, disposed at an angle to the lens. The filter is selected to permit the passage of the specific wavelength of the light emitted, and reflect or absorb all others. Several filters may be provided on the wheel, to permit sequential detection of light emitted from multiple reagents emitting light at different wavelengths.

The samples are fed to the optical detection platform through a loading device designed to work well with robotic and automated preparation systems. The well-plate, with reaction mixture already provided, is placed on a shuttle by a human, or preferably, robot. Alignment of the plate on the shuttle may be relatively coarse, notwithstanding the requirement for tight tolerances to match the collimator grid array. As the shuttle leaves the loading position, a resilient means urges the plate into strict conformal alignment. The shuttle positions the plate under an overhead injection bar, which may accommodate up to sixteen wells in a column at one time. If not previously added, a triggering agent or luminescent reagent is added to the sample wells, and the plate indexes forward to load the next column of wells across the plate. The shuttle then advances through a door into the sample chamber, and the plate is aligned with the collimator and the Fresnel lens. Since many reactions proceed better, or only, at elevated temperatures, the sample chamber is insulated, and provided with heating means, for heating the air in or provided to the chamber. In order to maintain temperature in the chamber close to room temperature and to accurately control temperature, the chamber may also be provided with a heat exchanger.

The light emission from the entire multiple well plate is imaged at once, with subsequent imaging through a different filter if multiple wavelengths are employed. The signal obtained is processed to further reduce crosstalk reduced by the collimator and the presence and amount of luminescence is quickly detected and calculated by a personal computer using automated software. Data is then reported as intensity per well or further analyzed relative to specific assay standards.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
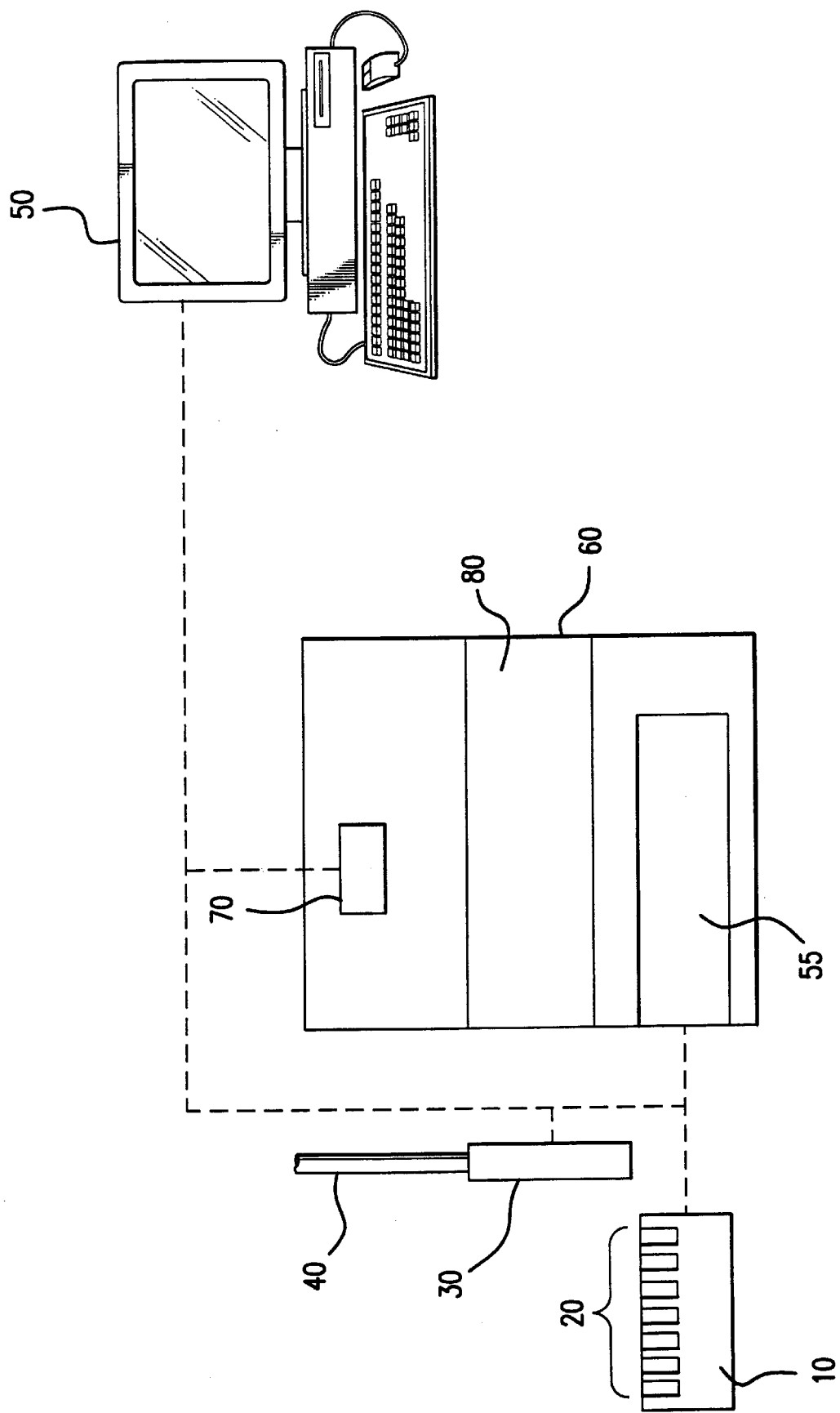
FIG. 1 is a cross section of a preferred embodiment of a luminescence detecting apparatus according to the present invention.

Referring now to the drawings, wherein like reference numerals designate identical or corresponding parts throughout the several views, and more particularly to FIG. 1 thereof, a preferred embodiment of the luminescence detecting apparatus of the present invention uses a shuttle or tray to carry a micro plate (plate) 10 comprising a plurality of sample wells 20 which may in the preferred embodiment number as many as 1,536 or more. Persons of ordinary skill in the relevant art will recognize that the number of sample wells 20 is limited only by the physical dimensions and optical characteristics of the luminometer elements, and not by the technology of the present invention. The sample wells 20 may be filled with analyte manually, or robotically, prior to delivery to the inventive apparatus. Agents necessary for chemiluminescence may be filled automatically via the injector 30, to which analyte is supplied through an array of supply tubes 40 or prior to placing the plate on the tray. Typically, the sample wells will contain chemiluminescent reagents. These reagents emit light at intensities proportional to the concentration of analyte in the sample. This light can be very low intensity and requires an instrument with sufficient sensitivity to achieve the desired detection limits.

The operation of injector 30 is controlled by central processor 50 which, in the preferred embodiment, may control the operation of all elements of the luminometer of the present invention. Data collection, analysis and presentation may also be controlled by the processor 50. Further in a preferred embodiment of the present invention, the injector 30 may also be used to add buffer solutions to the analytes and also to add reagents that enable "glow" and/or "flash" luminescence imaging, that is sustained or brief, intense emission, respectively, all under control of central processor 50.

After the analytes are placed in the sample wells 20, plate 10 is placed in sample chamber 55, which is located in optical chamber 60 at a fixed focal distance from and directly under the charge-coupled device (CCD) camera 70, in order to permit the CCD camera to image the luminescent sample accurately. The sample chamber 55 is preferably capable of precise temperature control, as many luminescent reagents and specific luminescent reactions are temperature dependent. Temperature control is provided by central processor 50, which can vary the temperature for each individual sample plate 10, as central processor 50 controls the movement and injection of the sample wells 20 in each sample tray 10. In a preferred embodiment of the luminometer of the present invention, central processor 50 also controls an industrial robot (not shown) which performs the activities involving analyte handling in the luminometer of the present invention.

With the plate 10 placed in the sample chamber 55, the optics 80 deliver the image of the complete microplate 10 as a single image to the CCD camera 70.

Although the operation of the luminometer of this invention is an integral, continuous practice, and all elements of the luminometer cooperate together to provide precise, accurate and reliable data, the invention may be more easily understood by reference to three separate, integrated systems, the optics system, the mechanical system and the processing system. Each is discussed in turn, with a discussion of examples of the operation as a whole to follow.

Optics System

Figure 2:
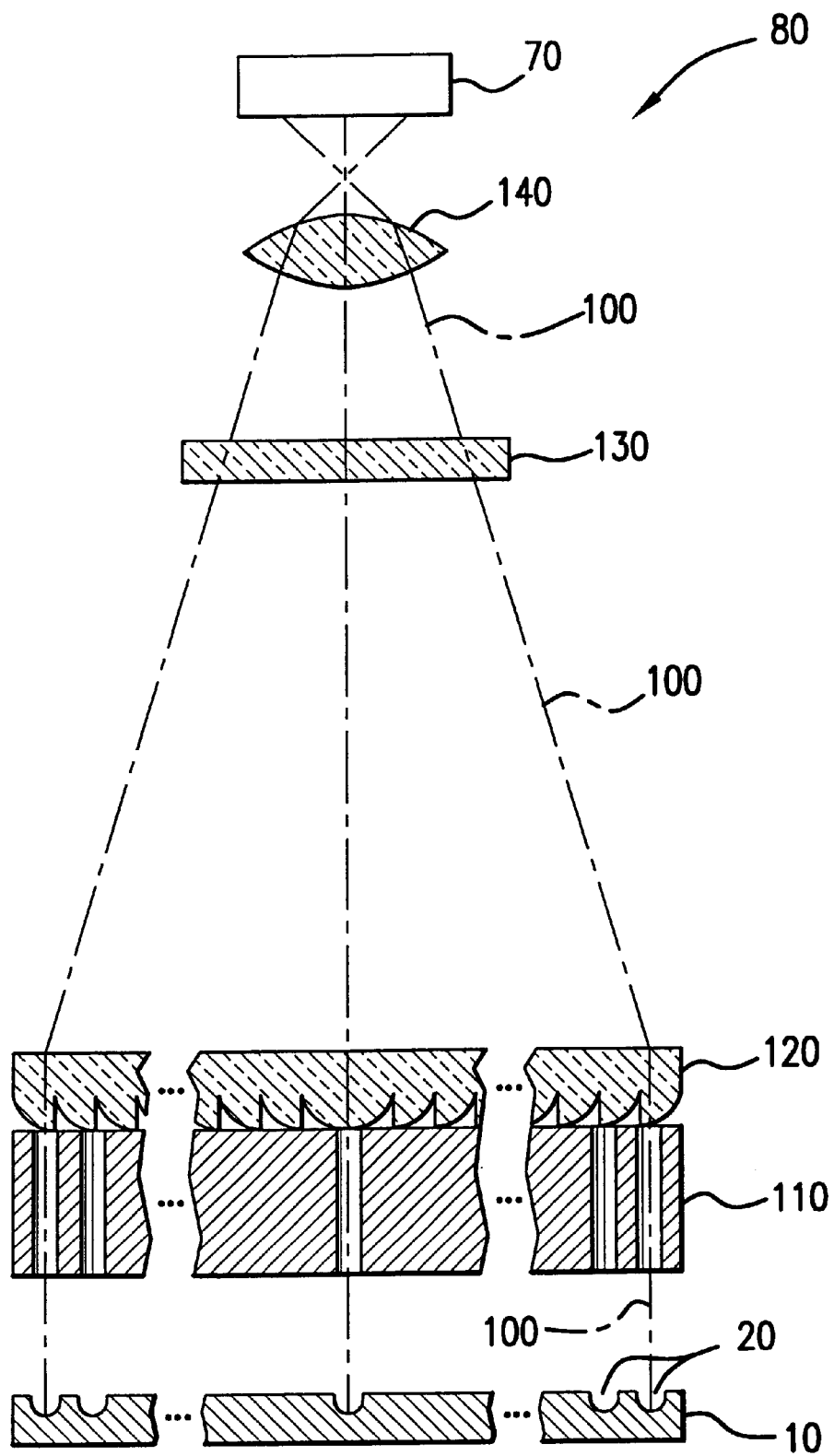
FIG. 2 is a detailed cross section of the optics of a luminescence detecting apparatus according to the present invention.

Turning now to FIG. 2, the optics 80 are shown in further detail. Luminescent emission 100 from the analyte in plate well 20 located in the plate 10 travels first through dark collimator 110, which permits only parallel and semi-parallel light rays to exit the sample wells 20 for eventual imaging by the CCD camera 70. The effect of collimation assists with the prevention of stray light from the sample wells 20 and with the elimination of crosstalk between luminescent samples. The collimator 110 may be sealably engaged, or in close proximity, to the sample tray 10, to enhance the restriction of stray light from the samples. Each well 10 is in strict registration and alignment with a corresponding grid opening in collimator 110. From the collimator 110, the luminescent radiation passes through a Fresnel field lens 120, which focuses the light toward camera lens 140. In a preferred embodiment of the present invention, the collimator 110 and Fresnel field lens 120 are packaged in a cassette that can be changed by the user. Such an equipment change may be necessitated by varying optical characteristics of different analytes and different well distributions in plates.

The use of a Fresnel field lens is preferable to alternative optical devices for several reasons. Initially, improvements in design and materials have capitalized on the superior optical capabilities of the Fresnel lens, while virtually eliminating its once inherent limitations. Today, many Fresnel lenses are made of molded plastic, creating an almost flawless surface with very little scatter light. The elimination of scatter light is an important element of eliminating crosstalk between adjacent samples in the luminometer of the present invention. Furthermore, improved types of plastics commonly employed in the manufacturing of Fresnel lenses and other optical devices have optical qualities equivalent to ground glass lenses.

Using high tech processes such as computer-controlled diamond turning, complex aspheric surfaces can be cut into a long lasting mold for casting Fresnel lenses. In this manner, Fresnel lenses can be manufactured to produce the precise optical imaging effect that is most efficient for a charge coupled device camera, as in the present invention. Also, Fresnel lenses offer an advantage over conventional lenses in that they can be molded flat and very thin. Because of the shape of the Fresnel lens, it can easily be integrated directly into the housing of the luminometer, enhancing the light-tight properties necessary for accurate imaging of low light samples. Furthermore, Fresnel lenses are much less expensive than comparable conventional glass lenses.

As with any other lens, the total beam spread from a Fresnel lens depends on the size of the source in relation to the focal length of the lens. Smaller sources, such as luminescent assay samples, and longer focal lengths produce more compact beams. Since there are practical limitations to minimizing the geometry and dimensions of the optics 80 in the luminometer of the present invention, the use of Fresnel field lens 120 provides the greatest opportunity for fine-tuned optics. The emissions from plate 10 pass through lens 120, and are refracted such that the image obtained at CCD 70 appears to look directly downward into all wells, even laterally displaced (edge) ones. This feature is typically called "telecentric."

Further in a preferred embodiment of the present invention, the filter 130 may be configured on a wheel, wherein different filter elements may occupy different portions of the wheel, depending on the luminescent characteristics of the sample being analyzed. Filter 130 is preferably inclined at an angle of 20°–30° relative to the CCD, so that stray reflected light is reflected outside the field of view. Specifically, the filter wheel 130 permits the selection of different wavelength ranges, which not only permit high quality imaging, but may be used to separate the emissions of different reagents emitting at different wavelengths. Again, the filter wheel 130 is controlled by central processor 50, in coordination with central processor 50's control of the individual sample wells 20 in the sample plate 10. In many assays, such as those addressed in pending U.S. patent application Ser. No. 08/579,787, incorporated by reference herein, multiple luminescent reagents, which emit at different wavelengths, are employed in a single well. Using multiple filters, each can be imaged in turn, and the true concentration can be calculated from the data set resulting using pre-stored calibration factors. Filter 130 is preferably provided with an infrared (IR) filter operating in conjunction with the selected bandpass, or as an independent element. Applicants have discovered that stray IR radiation, resulting from the plate phosphorescence, resulting in abnormally high backgrounds. An IR filter suppresses this.

From the filter wheel 130, the sample-emitted light passes through camera lens 140, which in the preferred embodiment is a large aperture, low distortion, camera lens. Camera lens 140 focuses the image of the sample on the CCD chip 70. In the preferred embodiment of the present invention, CCD camera 70 is a cooled, low noise, high resolution device. The lense is preferably a 35 mm wide angle lens with a low light level (F1.4) large aperture character. Magnification of 3–6, preferably about 5.5, is preferred. In preferred embodiments CCD camera 70 is provided with an anti-blooming CCD chip, to enhance dynamic range, which is about $10^5$ in the claimed invention, referred to as the NorthStar™ luminometer. Blooming occurs when a single pixel is overloaded with light and its photoelectrons overflow the CCD device well capacity, contaminating surrounding pixels. Further in the preferred embodiment of the luminometer of the present invention, the selected CCD camera includes a liquid cooled thermoelectric (Peltier) device providing cooling of the CCD to approximately −35° C., and the CCD has 1280×1024 pixels, each of which are 16 $\mu$m square, producing a total active area of 20.5 mm×16.4 mm. The quantum efficiency averages 15% over the range from 450 nanometers to 800 nm. The output is digitized to 16 bit precision and pixels can be "binned" to reduce electronic noise.

By using the features disclosed herein, the luminometer of the present invention has a spatial resolution capable of providing high quality imaging of high density sample trays. The noise performance and CCD temperature are designed to provide the desired detection limit.

Mechanics

Figure 3:
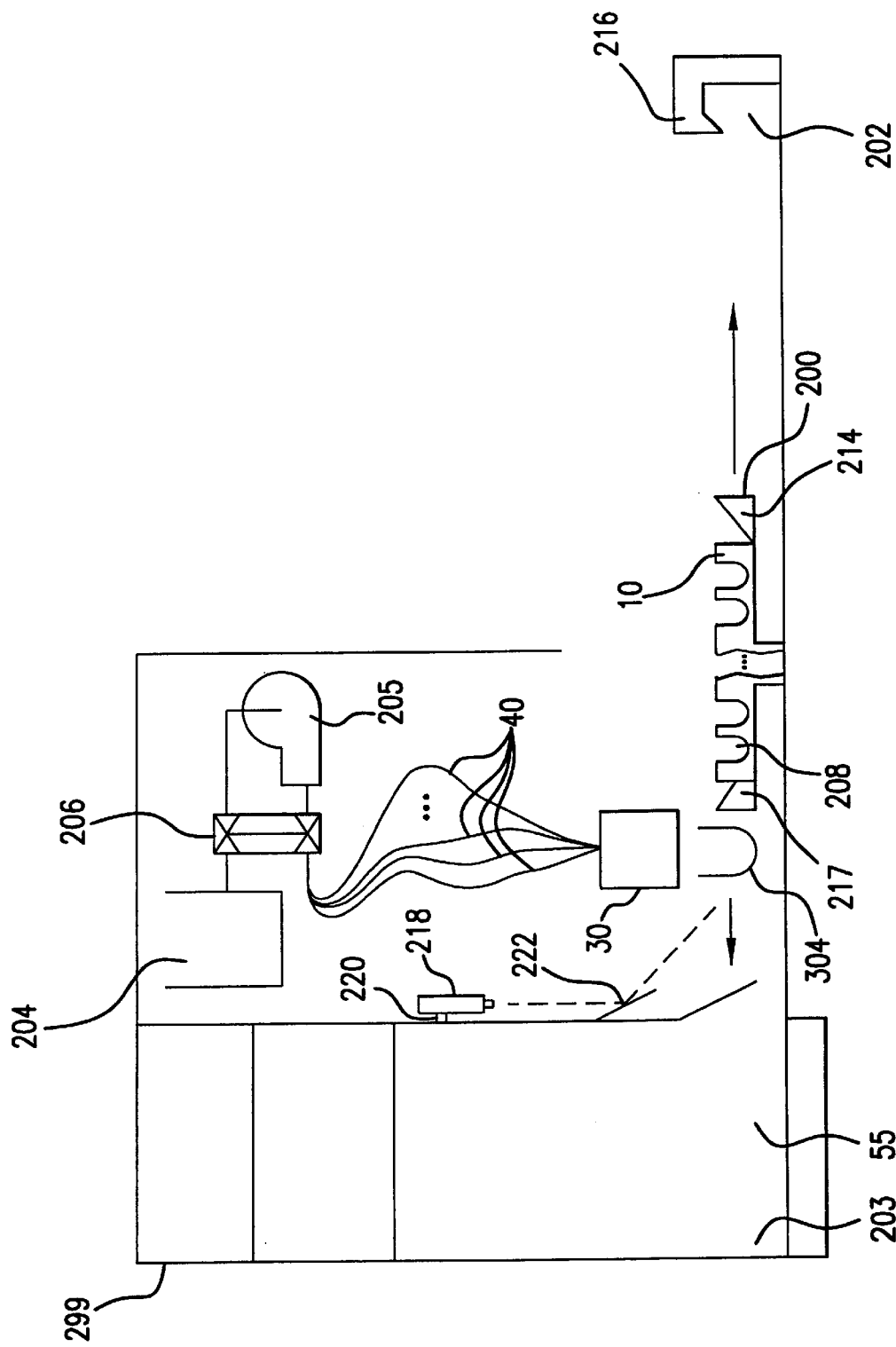
FIG. 3 is a cross-sectional view of the plate transport system of the invention.

The mechanical systems of the luminometer workstation of this invention are designed to achieve automated, high throughput precise delivery of microplates in registration with a collimator 110 so as to be read by the CCD Camera 70. To this end, as shown in FIG. 3, a cross-section of the inventive luminometer shuttle 200 translates from a load position 202, where plates 10 are loaded on to the shuttle, preferably by a robotic device such as robot arm, and the shuttle 200 then translates towards sample chamber 55, to read position 203. Shuttle 200 is caused to translate by a conventional stepper motor (not pictured). As shuttle 200 advances toward sample chamber 55, it may stop underneath injector 30. Injector 30 is more fully illustrated below in FIG. 4. Referring still to FIG. 3, injector 30 delivers fluid reagents drawn from reservoir 204. Syringe pump 205 draws the fluid reagents from reservoir 204, and pumps the fluid to the injector tubes 40. Two way valve 206 controls the passage of the fluid drawn by syringe pump 205 from reservoir 204 and pumped by syringe pump 205 to the supply tubes 40. In actual practice, there are as many injector tubes 40 as injection ports being used, and multiple syringe pumps 205 are also used. As will be shown below in FIG. 4, injector 30 has up to sixteen injection ports 302. The plates used in conjunction with the luminometer when injection is used are typically prepared with up to sixteen wells in a column. As the shuttle 200 advances plate 10 underneath injector 30, shuttle 200 stops so that the first column 208 of wells is directly aligned under injector 30. Precise amounts of analyte are delivered to the first set of wells, and shuttle 200 indexes forward one column, so as to inject reagent into the second column of wells 210. This process is repeated until all wells are filled. Thereafter, shuttle 200 advances forward into sample chamber 55 through hinged door 212. In the alternative, door 212 may be a guillotine door or similar type of closing mechanism. The wells of plate 10 are then read in sample chamber 55. Upon completion of reading, shuttle 200 translates back to load position 202.

Before shuttle 200 advances to the injection bar, it may be necessary to fully prime the tube with fluid, so as to provide for precise delivery into the plate. Trough 304 swings out from its storage position parallel to the direction of travel of shuttle 200, shown by an arrow, to a position directly underlying the injector 30, perpendicular to the direction of travel. Fluid in the injector and tubes 204 are delivered into trough 304, and removed by suction. Trough 304 then returns to its rest position, parallel to, and away from, the direction of travel of the shuttle 200, when the shuttle is moved toward the sample chamber 55. On its return trip to load position 202, locator 214 on shuttle 200 is engaged by cam 216. Locator 214 is mounted on a resilient means, such that when engaged by cam 216, the locator 214 recesses away from plate 10. This permits removal of plate 10, and delivery from a robotic arm or other source of a fresh plate 10, without the requirement of precise location. As shuttle 200 moves away from load 202, locator 214 is urged forward, firmly locating plate 10 in place. Plate 10 is held against shoulder 217 by the resilient urging of locator 214.

It is important that each plate be precisely identified, so that results are correlated with the correct test samples. In most HTS laboratories, most microplates are labeled with a unique "bar code." The label is often placed on the surface perpendicular to the plane of the plate itself. To permit precise identification of each plate, a bar code reader 218 is mounted on the luminometer housing generally indicated at 299 and directly above the door 212, for example on an arm or flange 220. Bar code reader 218 is focused on a mirror 222 which in turn permits reading directly off the front or leading edge of plate 10 as it approaches on shuttle 200. Thus, before each plate arrives in the sample chamber, its identity has been precisely recorded in processor 50, and the results obtained can be correlated therewith. Persons of ordinary skill in the art will recognize that a variety of configurations of alignment and placement of both bar code reader 218 and mirror 222 will result in the desired identification.

Figure 4:
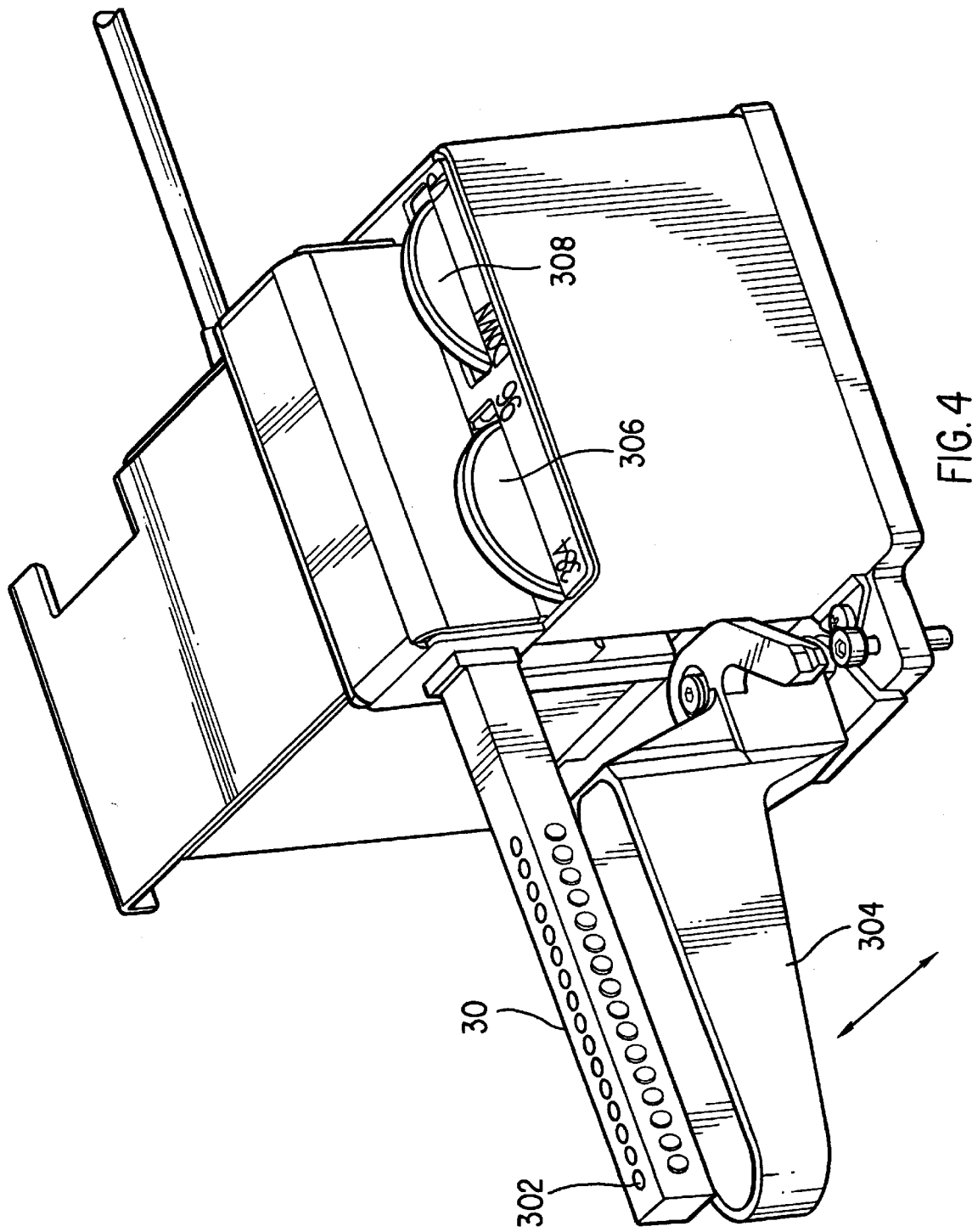
FIG. 4 is a perspective illustration of the injector arm assembly of the invention.

As more clearly shown in FIG. 4, injector 30 may be precisely located by operation of actuator wheel 306, provided with positions corresponding to the total number of wells on the plates being assayed. Similarly, the vertical position, to account for the different thicknesses of the plate, may be controlled by wheel 308. Given the simple translation movement of shuttle 200, and the precise locating and identification of each plate carried, rapid cycling of microplate test plates into and out of sample chamber 55 can be effected.

Figure 5:
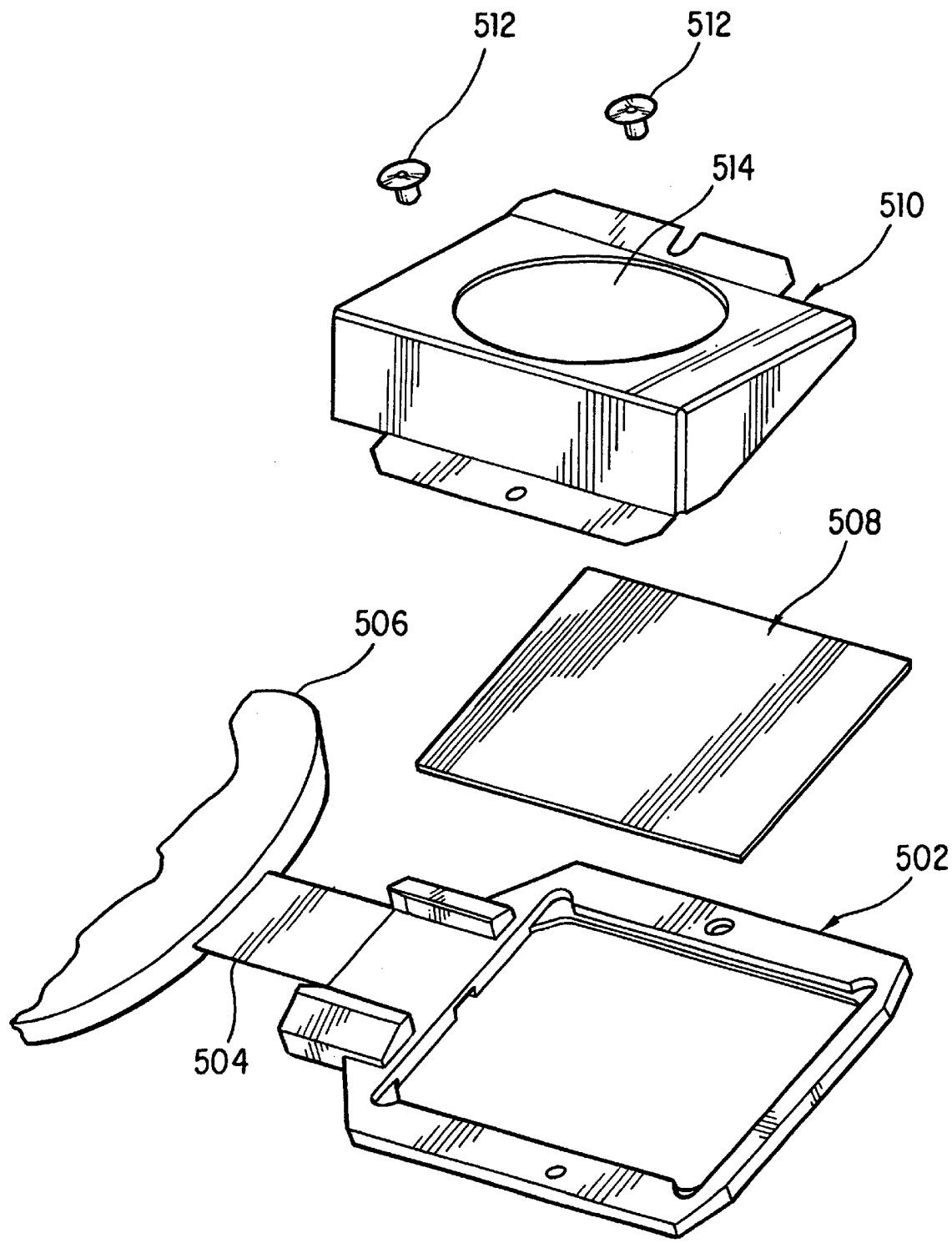
FIG. 5 is an exploded view of the filter wheel assembly.

As described above in connection with the optics system of the invention, a filter is provided which includes or reflects passage of light other than light falling within the selected wavelength of the luminescent emitter in use. The filter assembly is illustrated in exploded format in FIG. 5.

Filter frame 502 is supported by arm 504 which is connected to the hub of the filter wheel 506. Multiple different filters may be provided on a single wheel. The filter itself, 508, is securely mounted on the frame and held there by cover 510, which is secured to frame 502 by grommets, screws or other holding devices 512. As noted, filter wheel is positioned so as to hold filter 508 in frame 502 at in incline with respect to collimator 110, of about 22° nominally, so as to direct any reflections outside the field of view. Light passes through the filter opening 514, in alignment with camera lens 140 and CCD camera 70. As further noted above, filter 508 preferably includes an infrared block, either as a component of the filter itself, or as a component provided in addition to the filter for the measured light. An IR block is of value to prevent infrared emissions caused by extraneous radiation from altering the image received by the CCD camera.

Figure 6:
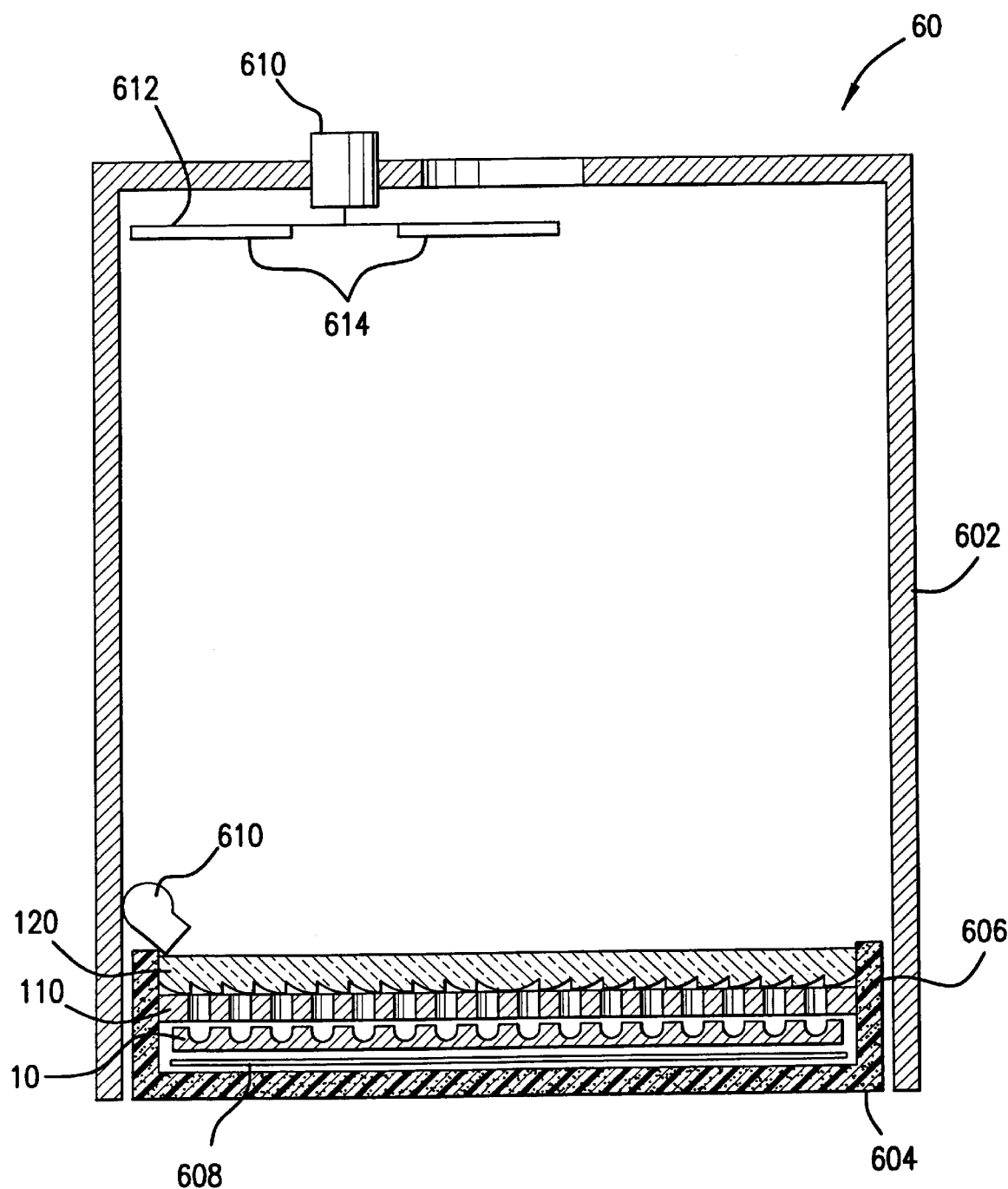
FIG. 6 is a cross-sectional view of the optical housing.

Optical chamber 60 is more fully illustrated in FIG. 6. As shown, optical chamber 60 is bounded by optical housing 602 in which fits sample housing 604. When a plate 10 is loaded into optical chamber 60, the plate is secured in sample housing 604 which is positioned in registry with collimator 110, over which is provided Fresnel lens 120. While many luminescent assays can be provided at ambient temperatures, some require elevated temperatures. The luminometer of this device is provided with a sample chamber in which the sample housing 604 carries insulation 606 which, in a preferred embodiment, is polyurethane foam, and heater element 608 to raise the temperature in the sample chamber 55 above ambient temperature, up to about 42° C.

There is a tendency, even at ambient conditions, for condensation to collect on the surface of the Fresnel lens 120, as a result of moisture coming from the filled wells of plate 10. The defogger 610 directs a stream of air heated just a few degrees, preferably about 2–3° degrees, above ambient conditions, or above the temperature of the chamber if the chamber is above ambient conditions, across the surface of the Fresnel lens 120, effectively preventing condensation. Mounted at the top of the interior of optical chamber 60 is filter motor 610 which drives filter wheel 612, on which may be mounted filters 614 of varying wavelength, for filtering undesirable wavelengths prior to imaging. Of course, a region is provided, indicated at 616, in the optical housing 602 of the optical chamber 60 for light to be directed onto the CCD camera after passing through the filter 614. The dimensions of optical chamber 60 are exaggerated in FIG. 6 to illustrate the relationship between the optical chamber 60 and the filter wheel 612, and defogger 610. In practice, the filter is located inside the optical chamber 60, and outside the sample housing 604 but alternate locations are possible while still achieving the desired function.

Figure 6A:
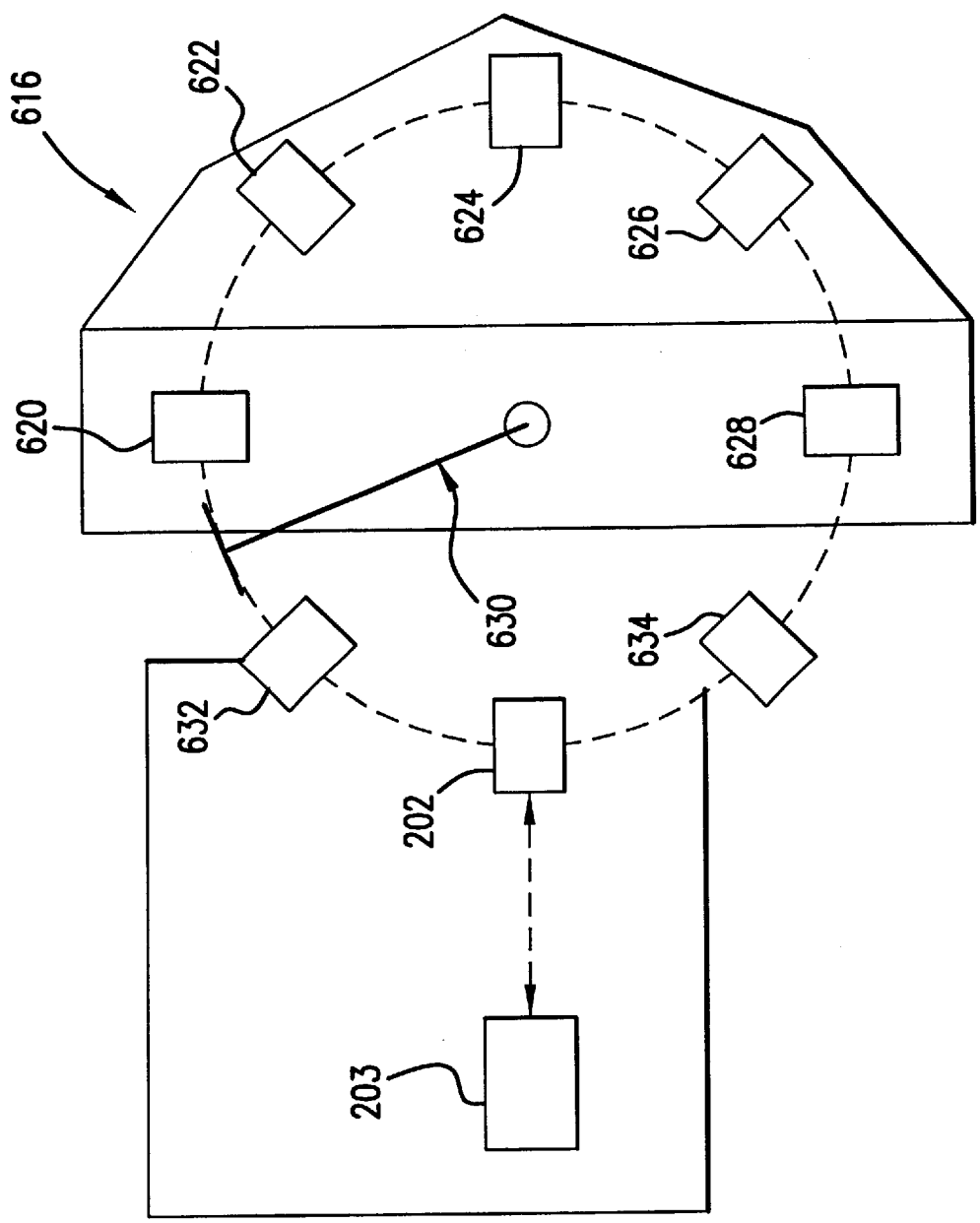
FIG. 6A is a plan view of a robotic mechanism of the invention.

In FIG. 6A, a plan view of a novel robotic mechanism 616 is displayed in a preferred embodiment of the present invention, which provides capacity for use in high throughput screening (HTS) applications. Referring to FIG. 6A, the operation is as follows: robot plate stacks 620, 622, 624, 626, and 628 each can be filled with multiple sample plates 10, arranged in a vertical stack. In the preferred embodiment of FIG. 6A, robot plate stack 628 is designated as the discard stack. The remaining robot plate stacks 620, 622, 624, and 626 can be programmed in order of delivery by software controlled by processor 50 (not shown). In order to load or pick plates from any of these stacks, robot arm 630 moves vertically and rotationally to the desired robot plate stack, under control of the software programmed in processor 50.

When commanded by processor 50, transport 200 of the instrument will move the sample plate 10 from load position 202 to the Read position 203, and return it to load position 202 when imaging is complete. In the embodiment of the invention shown in FIG. 6A, the elapsed time between moving the sample plate 10 from load position 202 to the read position 203, and returning it to load position 202 is typically 30–120 seconds, including imaging time.

Staging positions 632 and 634 are located at 45 degree positions relative to the position of robot arm 630. In one embodiment, while imaging is in process, the robot arm 630 can place a sample plate 10 at staging position 632, in preparation for placing the sample plate 10 in load position 202. When the imaging is complete, the robot can move the read plate from load position 202 to staging position 634, then load the plate from staging position 632 to load position 202, and while the sample plate 10 is being imaged, the robot can move the plate from staging position 634 to the discard stack 628, and place a new sample plate 10 at staging position 632. In practice, the staging positions are at approximately the same level as the load position, so movement is very quick. In the preferred embodiment, the robot arm 630 can do the time consuming moves to any of robot plate stacks 620, 622, 624, and 626 while imaging is going on, rather than in series with imaging.

With the staging positions 632 and 634, the cycle time for a single sample plate 10 is 2 moves from/to staging areas (3 seconds each), plus 2 transport moves IN/OUT to read position 203 (3 seconds each), plus the integration time (image exposure) time (typically 60 seconds), for a total cycle time of 72 seconds. Without using staging positions 632 and 634, the time would be 2 moves to stacks (30 seconds each), plus 2 transports (3 seconds each), plus the integration time (typically 60 seconds) for a total of 126 seconds. As described in the preferred embodiment of the robotic mechanism 616, the use of staging positions 632 and 634 decreases cycle time by 43%.

Processing

Figure 7:
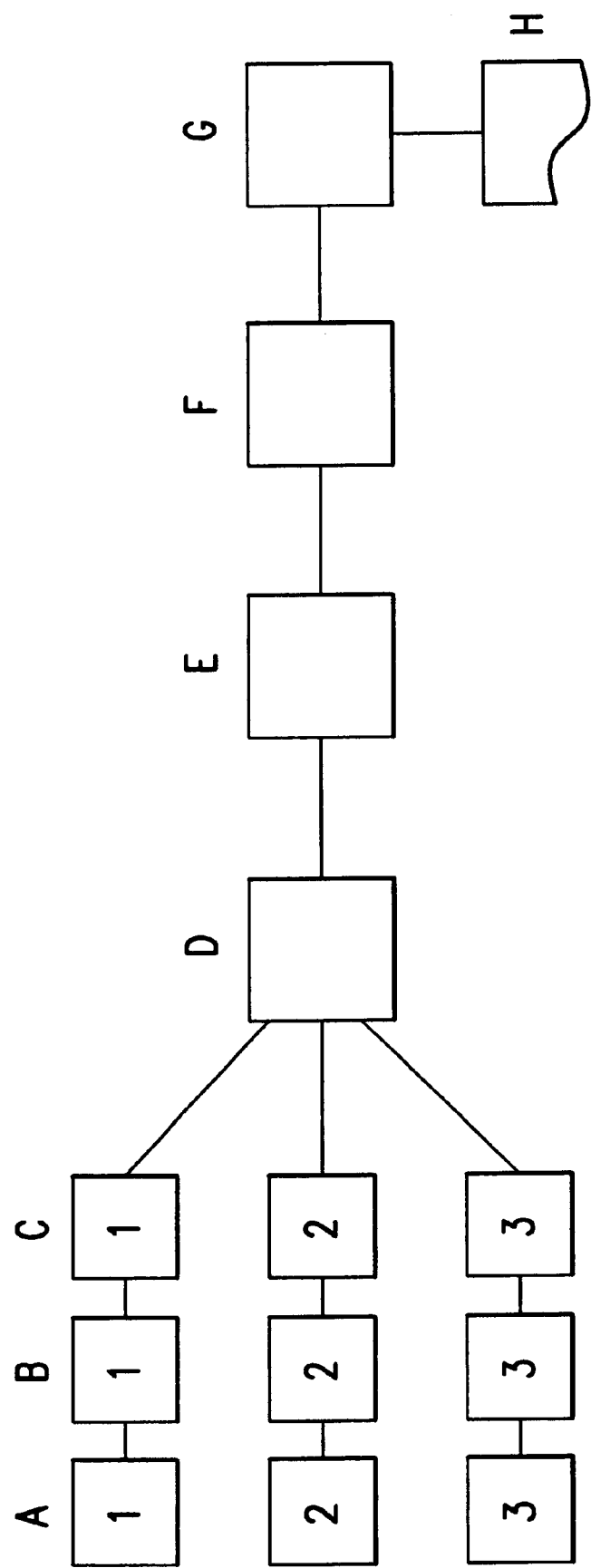
FIG. 7 is a flow chart illustration of the processing method of the invention.

As set forth above, the mechanical and optical systems of the luminometer workstation of the invention are designed to provide precise, quantified luminescent values in an HTS environment, taking advantage of the use of a Fresnel lens/collimator assembly to permit single image viewing by the CCD camera, and subsequent analysis. The collimator, the lens and the camera together combine to reduce crosstalk experienced in prior art attempts. The signals obtained are further processed, as illustrated in FIG. 7, through software loaded onto processor 50, or other convenient method, to further refine the values obtained.

Prior to processing image data collected through the integrated mechanical and optical systems of the invention herein described, the integrated processing component of the invention must first control the mechanical alignment of those integrated mechanical and optical systems for reliable data collection. This process is conducted under control of the processor 50. To conduct an alignment test, the luminescence detection of the present invention measures the light emitted from four test sample wells, called hot wells, of a test plate. In a preferred embodiment, the hot wells are located near each corner of the sample tray used for the alignment testing. The adjacent well crosstalk from each of the four hot wells is analyzed, and the values are compared. When the collimator is aligned precisely over the sample well tray, the crosstalk values will be symmetrical for the four hot wells. The software of the present invention flags any errors detected, such as incorrect number of test sample wells, incorrect intensity, or incorrect location. After the detection of no errors or after the correction of detected and flagged errors, the software of the present invention performs a symmetry calculation to determine precise alignment of the sample well tray, collimator, Fresnel lens and CCD camera assembly. In a known embodiment of the invention, known software techniques are employed to perform the symmetry calculation process by performing the following steps:

1. Extract the hot well and vertical and horizontal adjacent well intensities;
2. Calculate the averages of the horizontal and vertical adjacent well intensities separately for each hot well;
3. Calculate the differences between the actual adjacent intensity vs. the average for each of the horizontal and vertical directions;
4. Normalize the differences by the hot well intensity to convert to a percentage intensity value;
5. Find the worst case absolute value of the differences and display that as the overall misalignment;
6. Calculate the average X-direction (horizontal) misalignment by averaging the four adjacent wells to the right (horizontal direction) of the hot wells;
7. Calculate the average Y-direction (vertical) misalignment by averaging the four adjacent wells to the top (vertical direction) of the hot wells;
8. Calculate the rotational misalignment by averaging the left side hot well vertical adjacent wells at the top of the hot wells, and subtracting that from the average of the right side hot well vertical adjacent wells, thereby indicating any tilt in adjacent well values.

In order to clearly isolate and read each pixel, in step B, each image is subjected to "masking", a processing step whereby the edge of each well or corresponding light image is identified, or annotated, to set off and clearly separate each well region of interest, as disclosed in U.S. patent application Ser. No. 09/351,660, incorporated herein by reference. Again, masking is performed for each of $B_1$, $B_2$ and $B_3$, referring to the pre-cursor, full integration time image and post-cursor images, respectively. The images are then subjected to "outlier" correction, correcting or "shaving" outliers and anomalies. In this process, the pixels within the region of interest are examined to identify "outliers"—those that are in gross disagreement with their neighbors, in terms of light intensity detected, and if the intensity of a given pixel or small pixel area is significantly different than neighboring pixels or pixel areas, then the average of the surrounding pixels or areas is used to replace erroneous data. This can be due to random radiation, such as that caused by cosmic rays. In this process, this type of intensity is corrected.

Subsequently, in step C, each image $C_1$, $C_2$ and $C_3$ is subjected to dark subtraction, subtracting the dark background, so as to obtain average pixel values within each mask-defined region of interest. The subtraction is done on a well-by-well basis from stored libraries which are updated periodically.

Specifically, the dark subtraction is conducted to correct for the fact that even in the absence of light, CCD cameras can output low level pixel or bin values. This value includes the electronic bias voltage, which is invariant of position and integration time, and the "dark current," which may vary by position, and is proportional to integration time and to the temperature of the CCD. The CCD may also have faulty pixels that are always high level or saturated regardless of light input.

The processing software of the invention subtracts this background image or data from the real sample well image data in step C. As persons of ordinary skill in the relevant art will recognize, it is known to take a "dark" image immediately before or after a real image, imaging for the same integration time in both cases, and subtracting the "dark" image data from the real image data. In the preferred embodiment of the invention, "dark" image data is collected intermittently, preferably at specific time intervals. The initial "dark" image background data is collected at startup, and then typically at four hour intervals during image processing operations.

Because the background image has an integration time-invariant component and an integration time-variant component, data is collected for each sample well at minimum integration time and at maximum integration time, and a "slope/intercept" line is calculated between the two data points, using known data analysis techniques. This calculation permits data interpolation for any integration time between the minimum and maximum, and also permits data extrapolation for integration times below or beyond the minimum and maximum integration times.

In a preferred embodiment of the invention, a CCD camera is employed that has two separate "dark" current functions, caused by the CCD output amplifier. Operation of the amplifier generates heat and necessarily creates background "dark" image data. In the preferred embodiment, for integration times of less than 10 seconds, the amplifier operates continuously, whereas for integration times of more 10 seconds, the amplifier remains off until immediately prior to the read operation. The "slope/intercept" line calculated for integration times of more than 10 seconds will then necessarily have a lower slope than a "slope/intercept" line calculated for integration times of less than 10 seconds. In step C, the processing software element allows separate collection and least squares regression for both the 0 to 10 second integration time region and integration times that exceed 10 seconds. The "dark" background image data is stored separately for each individual AOI.

"Dark" current and bias can also vary over time. The processing software element corrects for this effect by comparing the integration time normalized (using the regression line technique described above) "dark reference" pixel values (outside the imaging field-described above), that were taken when the "dark" background images were taken, versus the "dark reference" pixel values taken while real sample well images are being taken. The difference between the values is then subtracted or added, as applicable, as a global number, to the "dark" background data. This corrects for bias drift and also for global CCD temperature drift.

As mentioned, all of the above "dark background" interpolation/subtraction of step C is done on a well by well basis.

At step D, if pixel saturation has occurred such that the average of the pre-cursor and post-cursor image must be used, the image data is multiplied by the reciprocal of the percentage represented by the pre-cursor images (e.g., 3%).

In step E, the well data is corrected for uniformity variations using a calibration file that is the reciprocal of the system response to a perfectly uniform input illumination.

In step F, the cross-talk correction is effected by processing the data as a whole and preparing a final image in much the same fashion as reconstruction of three dimensional images from a two dimensional data array is practiced.

Specifically in a preferred embodiment of step F, the impulse response function (IRF) is collected for all 96 wells of the 96 well plate type. This is done by filling one particular well in a given plate with a high intensity luminescent source, imaging the plate, and analyzing all of the wells in the plate for their response to the one high intensity well. The IRF is collected for all of the wells individually by repeating the process for every different well location desired for the complete data set. For 384 plate types, 96 sampling areas are selected, and data for the wells in between the selected sampled areas are interpolated in two dimensions. In the preferred embodiment, the 96 sampling areas comprise every second row and every second column, starting at the outside and working toward the center. Because in the 384 well plates the number of rows and columns is even, the two center rows and the two center columns are interpolated. The reflections in a 384 well plate are also modeled, and used to predict and interpolate reflections for the missing input data. Further in the preferred embodiment, all wells are normalized to the well with the highest intensity.

Subsequently in step F, the two-dimensional array of well IRF values for each well are "unfolded" into a one-dimensional column array, and the two-dimensional arrays of IRF values for other wells are added as subsequent columns, as shown in Chart 1 following:

Chart 1 - Unfolded Data Into Column 1

| IRF for A1 | IRF for B1 | IRF for C1 | |
|---|---|---|---|
| A1 | A1 | A1 | Etc |
| B1 | B1 | B1 | |
| C1 | C1 | C1 | |
| D1 | D1 | D1 | |
| E1 | E1 | E1 | |
| F1 | F1 | F1 | |
| G1 | G1 | G1 | |
| H1 | H1 | H1 | |
| A2 | A2 | A2 | |
| B2 | B2 | B2 | |
| C2 | C2 | C2 | |
| Etc | Etc | Etc | |

The unfolded matrix, which has the form of an N×N matrix, where N=the number of wells to be corrected, comprises a full characterization of the instrument crosstalk, including reflection factors. This unfolded matrix is then inverted, using known matrix inversion techniques, and used as a correction to matrix multiply a one-dimensional matrix unfolded from real assay data. This arithmetic process may be shown as matrix algebra:

[true source distribution]×[system $IRF$]=[instrument output]

solving for [true source distribution] produces

[true source distribution]={1/[system $IRF$]}×[instrument output]

Subsequently, the calculated well intensities resulting from the above processing are calibrated to an absolute parameter of interest, such as the concentration of a known reporter enzyme. This calibration is conducted through a normalization process producing any of a variety of calibration curves, which will be familiar to those of ordinary skill in the relevant art.

In optional step G, the processed image information is subjected to any necessary post adjustment processing, for appropriate correlation with the materials tested. Specifically, in a preferred embodiment, the processing software of the present invention is capable of performing multi-component analysis. The basic problem is to calculate separately the concentration of a single reagent in a single sample containing other different reagents. Typically, the reagents used with the invention are formulated so as to emit over different, but perhaps overlapping, spectrums. As earlier described with respect to the integrated optical element, the first step of separating the light from multiple reagents is accomplished by optical bandpass filters, which are designed to maximize the sensitivity of the target reagent emission, while minimizing the sensitivity to other non-target reagent emission. In the present embodiment of the invention, there is one optical filter for each target reagent emission spectrum.

Since optical filters are interference devices, their bandpass characteristics vary, dependent on the angle of incidence of the emission to be filtered. The angle of incidence will be unique for each well because each well's specific location is unique relative to the optical filter. Accordingly, all calculations and filter coeficients must be unique per sample well. The multi-component calibration is performed as follows:

Prior to the real multiplexed (multiple reagent) samples, standards containing only a single reagent in each well are imaged and analyzed. These standards will produce a set of coefficients to be used collectively as multi-component coefficients for each optical filter, for each well. For a given optical filter, the target reagent for that filter should produce the highest output. The other reagents may also. have spectra in the filter's bandpass, and will produce smaller outputs, which are a measure of the overlap of those nontarget reagent spectra into the filter signal. For example, the filter's output for the target reagent might be 850, and the filter's output for the other 2 reagents might be 100 and 50, respectively. If the 3 reagents were added together in a single well, the total output would be 1000, and the proportions would be 850:100:50. These coefficients are measured for each well location and filter separately, which gives a complete set of coefficients for simultaneous equations. This will allow a solution for any combination of concentrations of reagent in one sample well. Further in the preferred embodiment, these coefficients will also be normalized by the total intensity read in the "total emission" filter, so that the calculation will result in the same intensity as the instrument would measure if only a single reagent was measured by the "total emission" filter. This calculation may be shown as follows for a simple case of blue and green reagents (abbreviated as R in the calculations), and blue and green and total emission filters (abbreviated as F in the calculations):

Let $A$=(output of the instrument for blue $R$ thru the blue $F$)/(output of instrument for blue $R$ thru total emission $F$);

Let $B$=(output of the instrument for green $R$ thru the blue $F$)/(output of instrument for green $R$ thru total emission $F$);

Let $C$=(output of the instrument for blue $R$ thru the green $F$)/(output of instrument for blue $R$ thru total emission $F$);

Let $D$=(output of the instrument for green $R$ thru the green $F$)/(output of instrument for green $R$ thru total emission $F$);

These coefficients are measured for each well prior to running a multi-color run. Then for a multi-reagent/color run, (output of the instrument for the blue $F$)=$A$×(true intensity of blue $R$)+$B$×(intensity of green $R$);

and (output of the instrument for the green $F$)=$C$×(true intensity of blue $R$)+$D$×(intensity of green $R$)

These 2 simultaneous equations are then solved for the true intensity of the blue and green reagents by the processing software, under control of processor 50.

Further in step G, the raw output of the instrument for each filter is normalized for integration time before solving the equations. The resulting intensities could then be calibrated as concentration by use of standards as described in the previous section.

Finally, in step H, the analyzed data is presented in a user-acceptable format, again controlled by processor 50.

The invention may be further understood by reference to examples of assays practiced in HTS format, demonstrating the dynamic range and flexibility of the NorthStar™ luminometer.

EXAMPLES

Example 1

Figure 8:
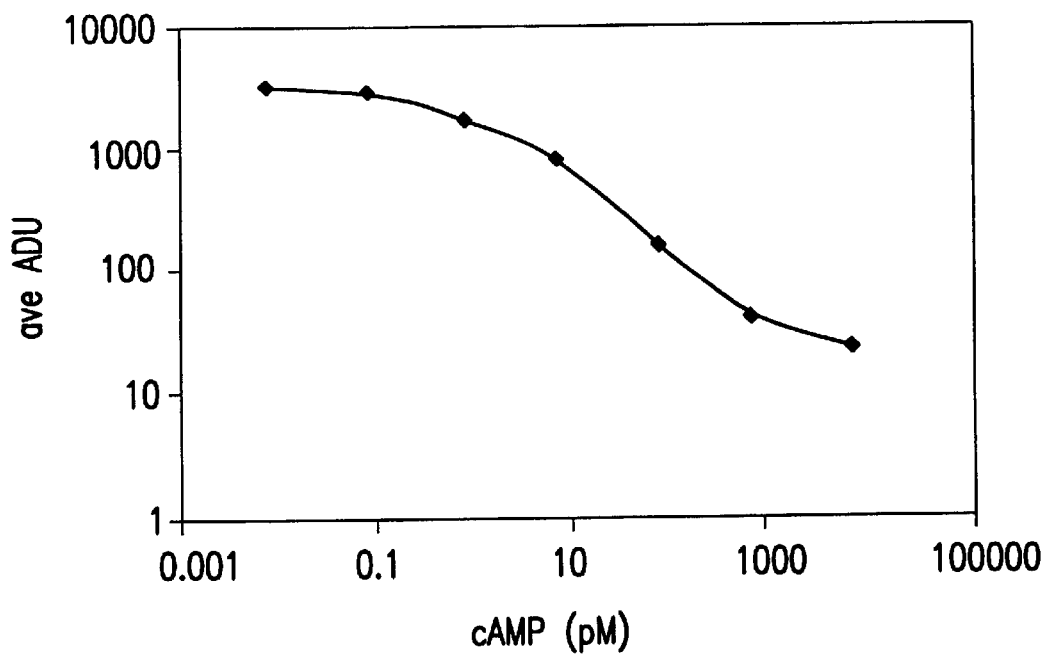
FIGS. 8–15 are illustrations of the results obtained using the invention in Examples 1–10, respectively.

Purified cAMP Quantitation cAMP standards were serial diluted and added to a 96-well assay plate with alkaline phosphatase conjugated cAMP and anti-cAMP. Plates were processed with the cAMPScreen™ protocol and imaged for 1 minute on the NorthStar™ 30 minutes after addition of CSPD®/Sapphire-II™. A sensitivity of 0.06 pM of purified cAMP is achieved with cAMP-Screen™ on the NorthStar™ workstation. The results are depicted in FIG. 8.

Example 2 cAMP Induction in Adrenergic β2 Receptor-expressing C2 Cells

Figure 9:
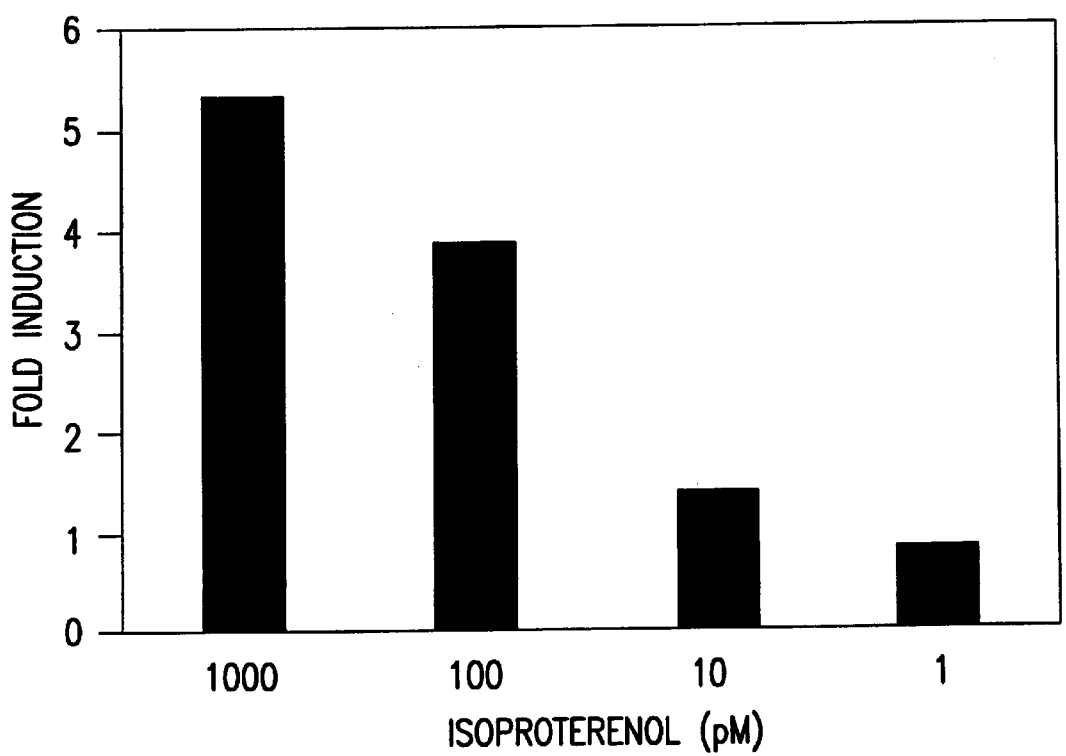

Adrenergic β2 Receptor-expressing C2 cells were plated in a 96-well plate (10,000 cells/well) and stimulated with isoproterenol for 10 minutes. cAMP production was quantitated in cell lysates using the cAMP-Screen™ assay. The assay plate was imaged for 1 minute on the NorthStar™, 30 minutes after addition of CSPD®/Sapphire-II™. Increasing cAMP levels were detected on the NorthStar™ from the stimulated adrenergic receptor. The results are depicted in FIG. 9.

Example 3

Figure 10:
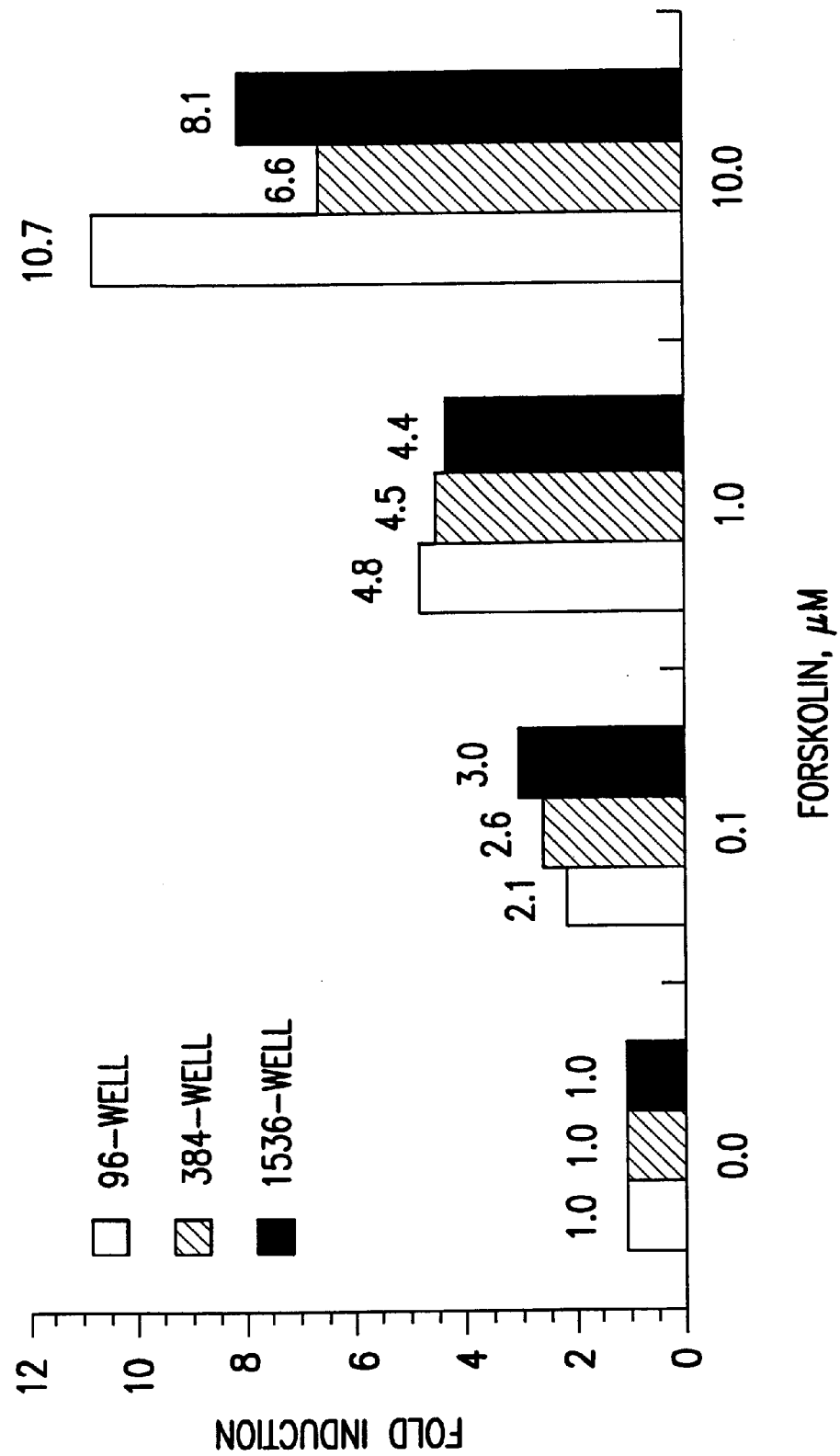

Luc-Screen™ Reporter Gene Assay in 96-, 384- and 1,536-well Format pCRE-Luc-Transfected cells were seeded in 96-, 384- and 1,536-well plates, incubated for 20 hours with forskolin, and assayed with the Luc-Screen™ system. PCRE-Luc contains the luciferase reporter gene under the control of a cAMP response element (CRE). Forskolin induces intracellular cAMP production through the irreversible activation of adenylate cyclase. All plate formats demonstrate comparable forskolin-induced cAMP levels. The results are depicted in FIG. 10.

Example 4

Figure 11:
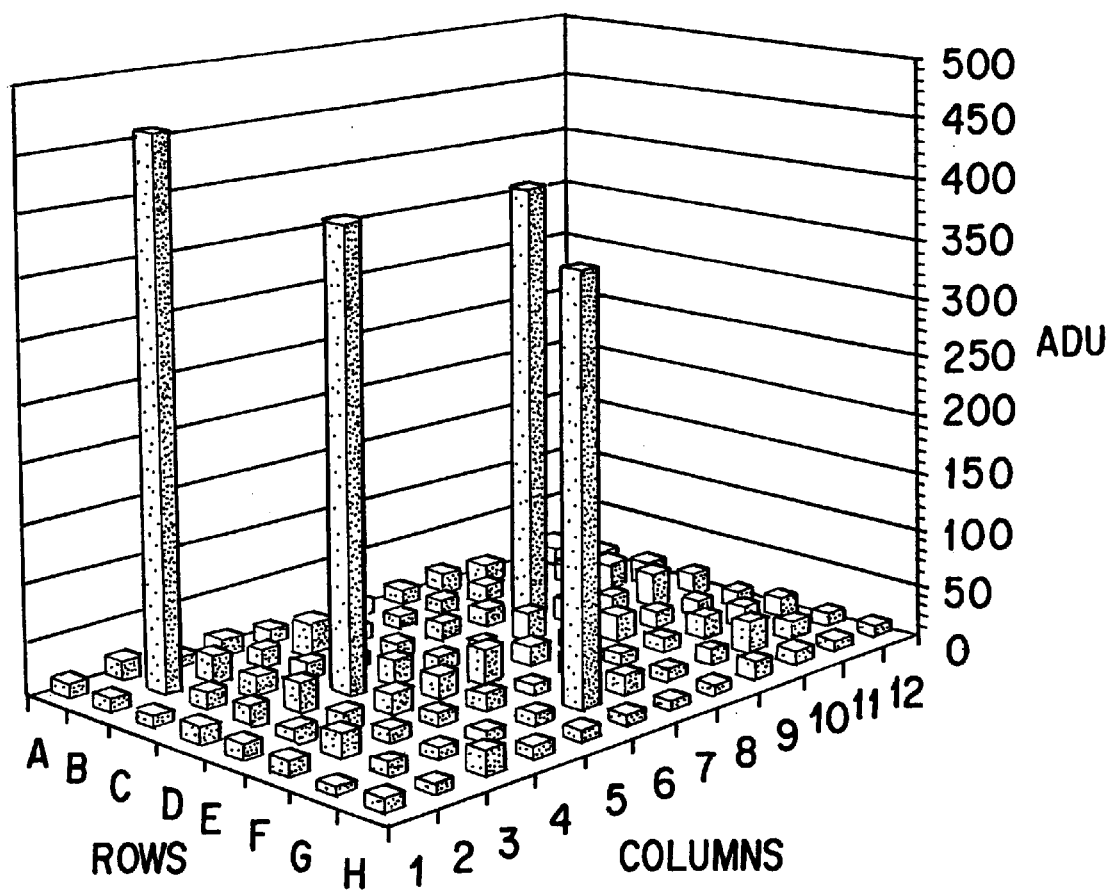

Forskolin Induction of pCRE-Luc Transfected NIH-3T3 Cells pCRE-Luc-Transfected cells were seeded in a 96-well plate. Four random wells were induced for 17 hours with 1 mM forskolin and the entire plate was assayed with the Luc-Screen™ system. The results are shown in Figure 11.

Example 5

Dual-Light® Quantitation of Luciferase & β-glactosidase Reporter Enzymes

Figure 12:
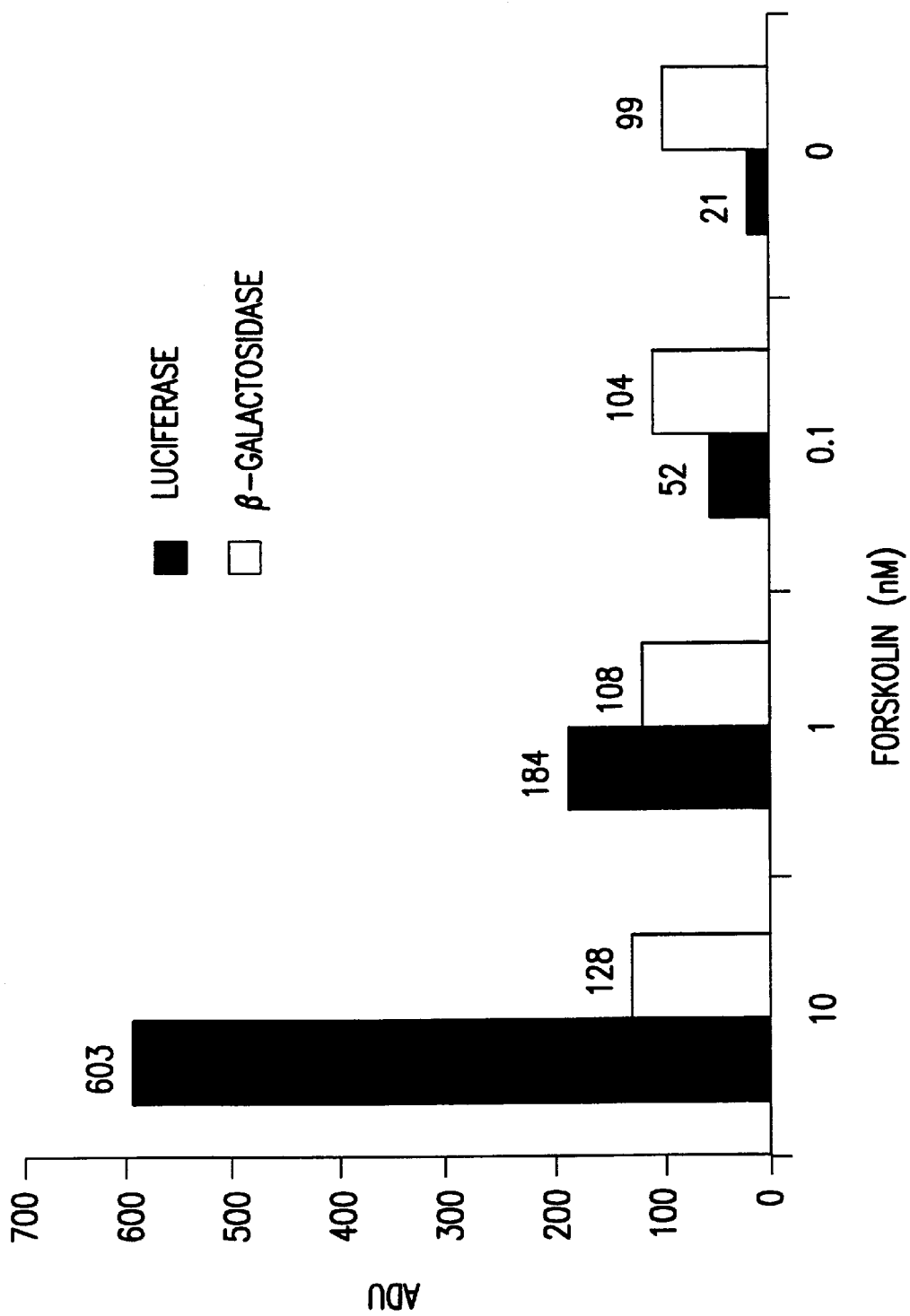

NIH/3T3 cells were co-transfected with pCRE-Luc and pβgal-Control, and seeded into a 96-well microplate ($2 \times 10^4$ cells/well). Cells were incubated with forskolin for 17 hours. Modified Dual-Light® Buffer A was added to cells and incubated for 10 minutes. Modified Dual Light® Buffer B was injected and luciferase-catalyzed light emission was measured immediately. Thirty minutes later, Accelerator-II was added, and then β-galactosidase-catalyzed light emission was quantitated on the NorthStar™ HTS workstation. Quantitation is shown graphically in FIG. 12.

Example 6

Normalized Fold Induction of Luciferase Reporter

Figure 13:
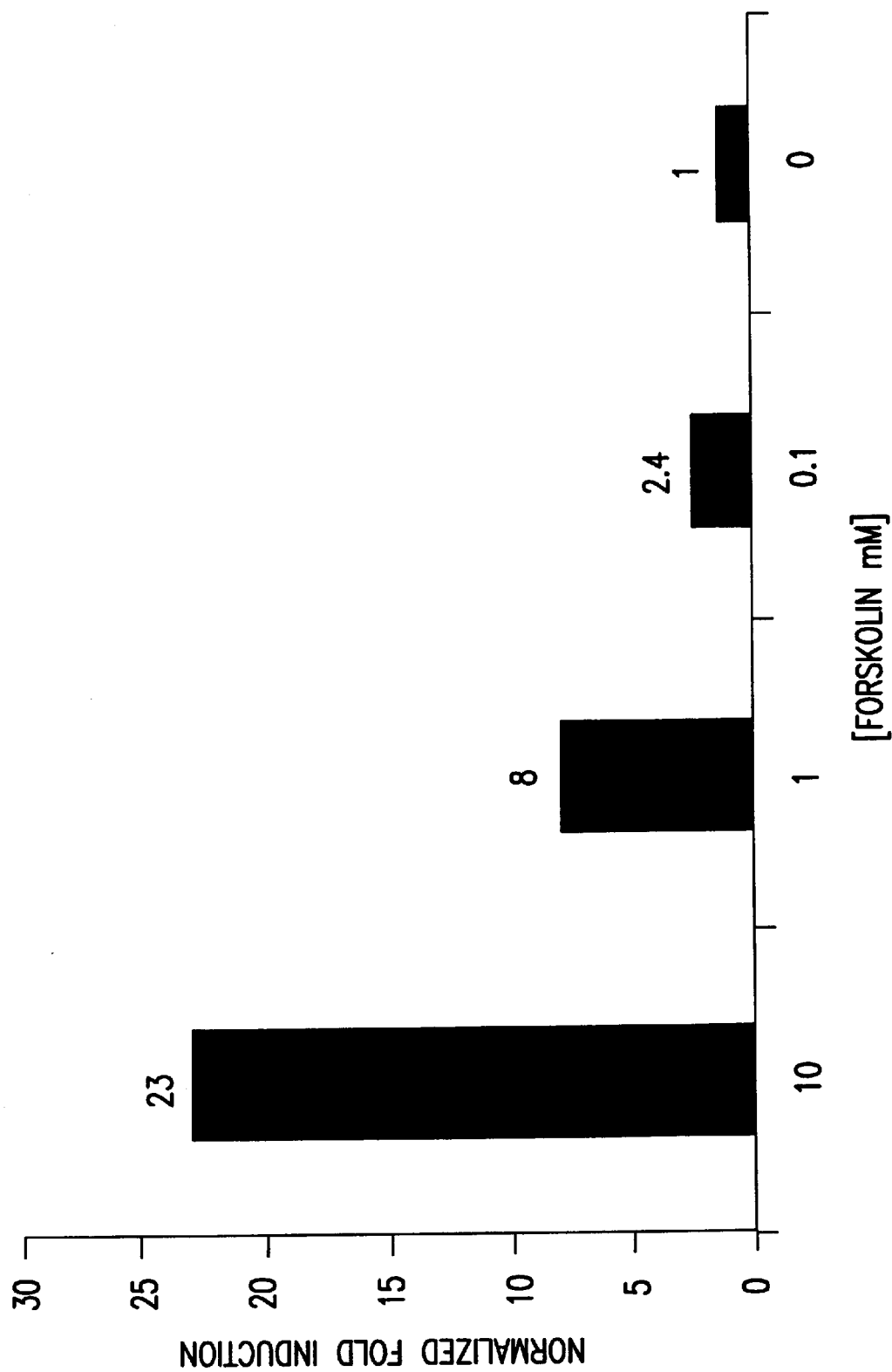

Fold induction of luciferase activity was calculated following normalization to β-galactosidase activity. The Dual-Light® assay enables the use of a control reporter for normalization, or to monitor non-specific effects on gene expression. This is depicted in FIG. 13.

Example 7

Effect of BAPTA-AM on Antagonist Activity

Figure 14:
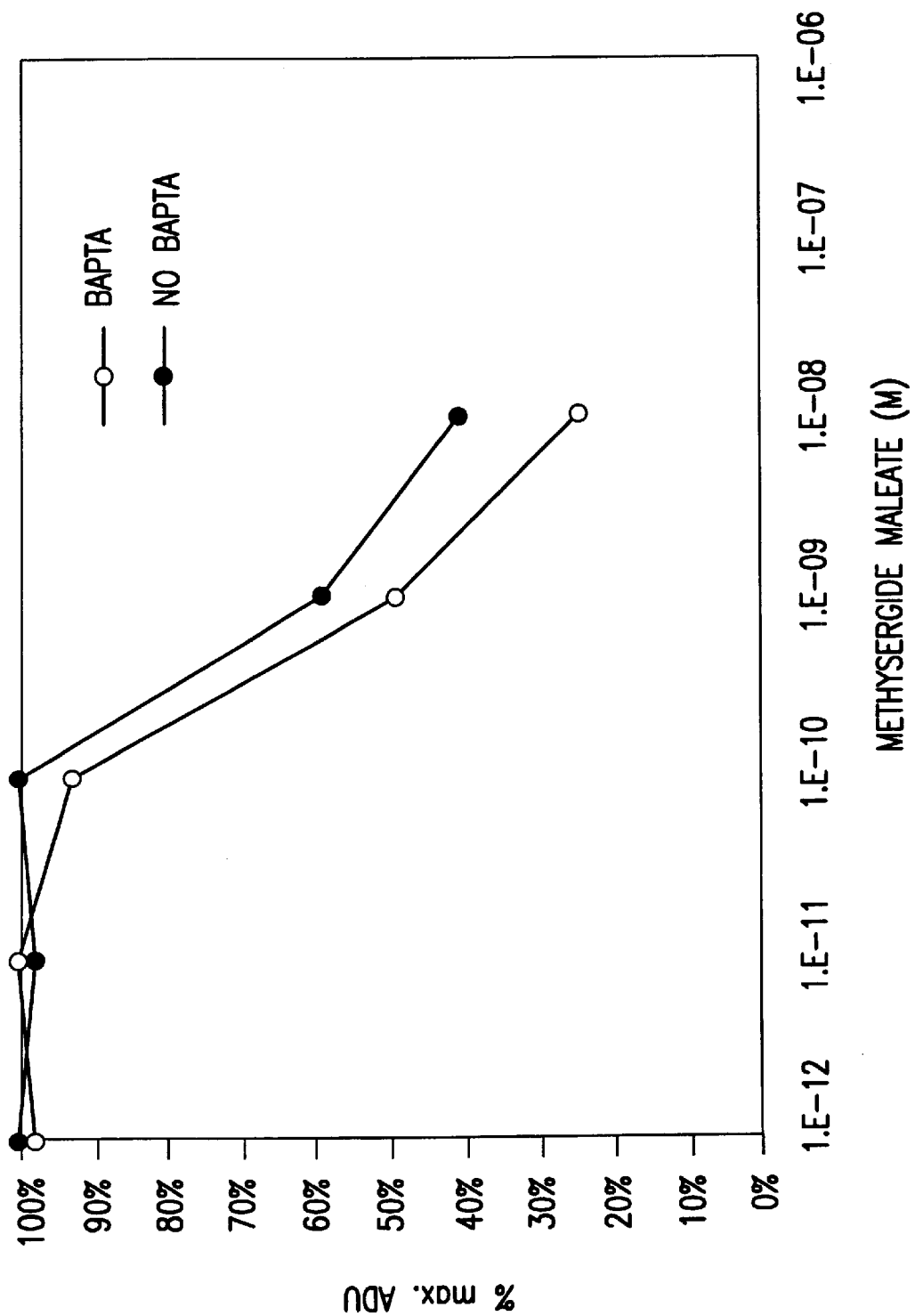

CHO-Aeq-5HT2B cells were loaded with coelenterazine h+/−0.5 $\mu$M BAPTA-AM for 4 hours. The antagonist methysergide was added to the charged cells for 30 minutes. 1 $\mu$M agonist a-Me-5HT was injected, and the emitted light was integrated for 20 seconds on the NorthStar™ system. The reported IC50 for methysergide (0.6 nM) is unchanged in the presence of BAPTA-AM. The data obtained appears in FIG. 14.

Example 8

Effect of BAPTA-AM on Peptide Agonist Stimulated of the Orexin 2 Receptor

Figure 15:
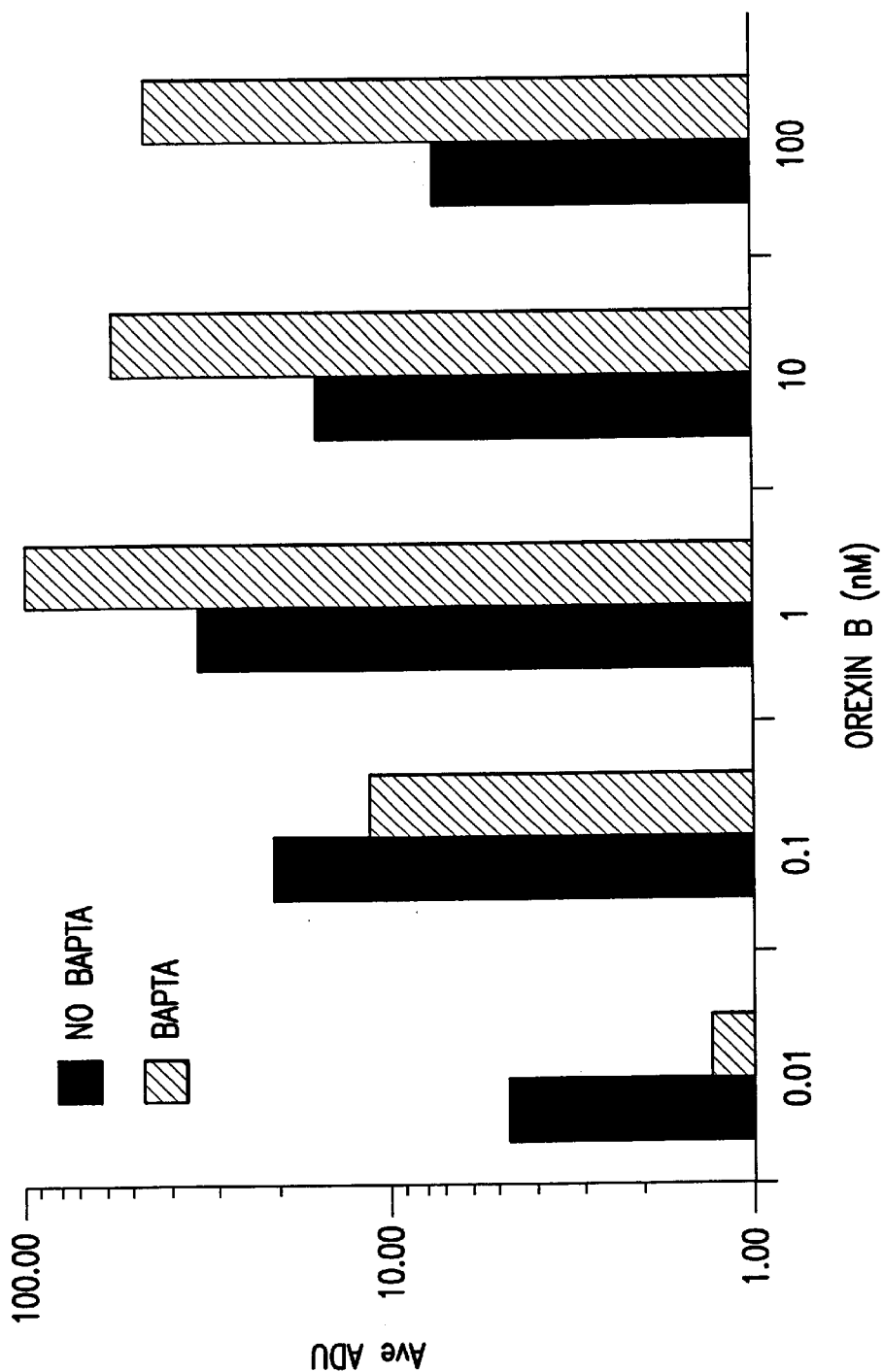

CHO-Aeq-OX2-A2 cells (Euroscreen) were loaded with coelenterazine h+/−0.6 $\mu$M BAPTA-AM for 4 hours. The peptide agonist Orexin B was injected into the wells, and the emitted light was integrated for 20 seconds on the NorthStar™. Using this assay on the NorthStar™ system, the reported EC50 for Orexin B (0.75 nM) is unchanged in the presence of BAPTA-AM. This is shown in FIG. 15.

This invention has been described generically, by reference to specific embodiments and by example. Unless so indicated, no embodiment or example is intended to be limiting. Alternatives will occur to those of ordinary skill in the art without the exercise of inventive skill, and within the scope of the claims set forth below.

What is claimed is:

1. An imaging system, comprising:
   a charge coupled device;
   a collimator;
   a Fresnel lens positioned between the collimator and the charge coupled device; and
   a camera lens positioned between the Fresnel lens and the charge coupled device;
   wherein the collimator, the Fresnel lens and the camera lens are arranged such that luminescent emissions from a source passing through the collimator toward the charge coupled device are refracted by the Fresnel lens and focused by the camera lens onto the charge coupled device to form an image of the source.

2. The imaging system of claim 1, further comprising at least one optical bandpass filter positioned between the Fresnel lens and the camera lens.

3. The imaging system of claim 2, wherein the optical bandpass filter is inclined at an angle with respect to the charge coupled device.

4. The imaging system of claim 3, wherein the optical bandpass filter is inclined at an angle of 20° to 30° relative to the charge coupled device.

5. The imaging system of claim 1, further comprising an infrared filter positioned between the Fresnel lens and the charge coupled device.

6. A luminometer comprising:

the imaging system of claim 1;

an optical housing;

a sample housing;

a shuttle adapted to move a sample plate from a load position to a read position in a sample housing;

a central processor adapted to collect and analyze image data from the charge coupled device;

wherein the charge coupled device and the camera lens are mounted outside of the optical housing and the collimator and the Fresnel lens are mounted inside of the optical housing and wherein the optical housing comprises a region which allows the passage of light such that luminescent emissions from a sample plate in the read position can pass through the collimator and the Fresnel lens and can be focused on the charge coupled device by the camera lens.

7. The luminometer of claim 6, further comprising an optical bandpass filter mounted inside of the optical chamber between the region which allows the passage of light and the Fresnel lens.

8. The luminometer of claim 7, wherein the optical bandpass filter is part of a filter assembly comprising a plurality of optical bypass filter elements.

9. The luminometer of claim 8, wherein the filter assembly is a filter wheel comprising a hub and a plurality of radially extending arms and wherein each of the plurality of optical bypass filter elements are mounted to one of the arms.

10. The luminometer of claim 9, further comprising a motor engaged with the hub of the filter wheel, wherein the motor is adapted to rotate the filter wheel to position any one of the plurality of filter elements between the charge coupled device and the Fresnel lens.

11. The luminometer of claim 6, further comprising a defogger adapted to direct a stream of heated air across a surface of the Fresnel lens.

12. The luminometer of claim 6, further comprising a heater adapted to heat a sample mounted in the sample housing.

13. The luminometer of claim 6, further comprising an injector including a plurality of injector ports, wherein the injector is adapted to draw a fluid from a reservoir and deliver the fluid through the injector ports to one or more sample wells on the sample plate.

14. The luminometer of claim 13, further comprising one or more pumps adapted to draw the fluid from the reservoir and deliver the fluid from the reservoir to the injector ports.

15. The luminometer of claim 14, further comprising a two-way valve, wherein the two way valve is adapted to control the passage of fluid drawn from the reservoir and/or delivered to the injector ports.

16. The luminometer of claim 13, further comprising a plurality of injector tubes, each of the injector tubes adapted to convey the fluid from the reservoir to an injector port.

17. A method of determining the mechanical misalignment of a sample tray in the luminometer of claim 6, wherein the sample tray comprises a plurality of sample wells arranged in a grid of rows and columns, the method comprising:

placing a luminescent composition in at least two hot wells in a first column of the sample tray and in at least two hot wells in a second column of the sample tray, wherein each of the hot wells are located near a corner of the grid and wherein each hot well is surrounded by four adjacent sample wells, two adjacent sample wells in the same column and two adjacent sample wells in the same row, and wherein the four adjacent sample wells do not contain the luminescent composition;

loading the sample tray onto the shuttle in the load position;

moving the sample plate into the read position with the shuttle;

imaging the sample tray with the charge coupled device;

collecting the image data on the central processor;

calculating the average misalignment of the sample tray in a first direction by averaging the intensity attributed by the charge coupled device to the wells adjacent to each of the hot wells in the first direction, the first direction corresponding to a column or row of the sample tray;

calculating the average misalignment of the sample tray in a second direction perpendicular to the first direction by averaging the intensity attributed by the charge coupled device to the wells adjacent to each of the hot wells in the second direction;

calculating the rotational misalignment of the sample tray by: averaging the intensity attributed by the charge coupled device to the adjacent wells in the same column for each of the two hot wells in the first column; averaging the intensity attributed by the charge coupled device to adjacent wells in the same column for each of the two hot wells in the second column; and calculating the difference between the averages determined above, wherein the difference is a measure of the rotational misalignment.

18. The method of claim 17, further comprising determining the overall misalignment of the sample tray in the luminometer by, for each of the hot wells:

measuring the intensity of luminescent emissions attributed by the charge coupled device to the hot well;

measuring the intensity of luminescent emissions attributed by the charge coupled device to each of the two adjacent sample wells in the same column and to each of the two adjacent sample wells in the same rows;

calculating an average for the intensity values for the two adjacent wells in the same column and an average for the intensity values for the two adjacent wells in the same row;

calculating the difference between the actual intensity attributed by the charge coupled device to each of the two adjacent wells in the same column to the average intensity for the two adjacent wells in the same column;

calculating the difference between the actual intensity attributed by the charge coupled device to each of the two adjacent wells in the same row to the average intensity for the two adjacent wells in the same row;

normalizing the differences by dividing the differences by the respective hot well intensity and, optionally, converting the result to a percentage; and taking the absolute value of the normalized differences;

wherein the largest absolute value is a measure of the overall misalignment of the sample tray.

19. The method of claim 17, further comprising adjusting the read position of the shuttle to the luminometer to reduce the rotational misalignment and/or the average misalignment of the sample tray in the first and second directions of the sample trays.

20. A method for high throughput screening of a plurality of sample trays in the luminometer of claim 6, wherein each of the sample trays comprises a plurality of luminescent samples, the method comprising screening a plurality of sample trays in succession, each sample comprising a plurality of samples, wherein, for each sample tray, the method further comprises:

loading the sample tray onto the shuttle in the load position;

moving the sample plate into the read position with the shuttle;

taking at least one image of the sample tray with the charge coupled device at an integration time;

collecting the image data generated by the charge coupled device on the central processor;

processing the image data; and removing the sample tray from the luminometer.

21. The method of claim 20, wherein the step of taking at least one image comprises:

taking a first precursor image of the sample tray with the charge coupled device at a first integration time;

taking a second full integration time image of the sample tray with the charge coupled device at a second integration time greater than the first integration time; and taking a third post cursor image of the sample tray with the charge coupled device at a third integration time less than the second integration time;

analyzing the full integration time image data with the central processor to determine if more than six pixels are saturated;

if more than six pixels of the full integration time image are saturated, using the full integration time normalized average of the pre and post cursor image data for subsequent processing; and if six or fewer pixels are saturated, using the full integration time image data as the image data for subsequent processing.

22. The method of claim 20, wherein the step of processing the image data on the central processor comprises a process selected from the group consisting of:

subjecting the image data to masking to extract the data for each particular well;

subjecting the image data to outlier shaving;

subjecting the image data to dark subtraction;

correcting the image data for uniformity variations in the charge coupled device and optical system;

correcting the image data for cross-talk from adjacent wells;

calibrating the image data to a parameter of interest;

subjecting the image data to post adjustment processing; and combinations thereof.

23. The method of claim 22, wherein the step of outlier shaving comprises:

identifying outliers by comparing the light intensity for a pixel or pixel area to the light intensity for neighboring pixels or pixel areas, wherein outliers have a light intensity that is significantly different than the neighboring pixels or pixel areas; and for each outlier identified, calculating the average intensity value for the neighboring pixel or pixel areas of each outlier and substituting the average value of intensity of the neighboring pixel or pixel areas for the intensity data of the outlier.

24. The method of claim 22, wherein the step of subjecting the image data to dark subtraction comprises:

collecting. dark image data for the luminometer at a first integration time and a second integration time before imaging a sample plate;

calculating a slope/intercept line for the two points using least squares regression;

normalizing the dark image data for the integration time of the image using the slope/intercept line; and subtracting the integration time normalized dark image data from the image data.

25. The method of claim 24, wherein dark image data is collected before imaging the first sample plate and periodically during high throughput screening, the method further comprising subtracting the integration time normalized dark image data calculated from the most recently collected dark image data from the image data.

26. The method of claim 22, wherein the step of correcting the image data for cross-talk comprises:

for each sample well on a sample plate, filling the sample well with a luminescent compound, imaging the sample plate, collecting the intensity data for the sample plate, forming a two dimensional array from the intensity data, and unfolding the two-dimensional array into a one dimensional column array;

forming a two-dimensional array from the column arrays for each sample well on the sample plate;

mathematically inverting the two-dimensional array;

unfolding the image data to form a one dimensional matrix; and multiplying the unfolded image data by the inverted two-dimensional array.

27. The method of claim 22, wherein the step of correcting the image data for cross-talk comprises:

for each sample well in a first set of selected sample wells on a sample plate, filling the sample well with a luminescent compound, imaging the sample plate; collecting the intensity data for the sample plate; forming a two dimensional array from the intensity values and unfolding the two-dimensional array into a one dimensional column array;

for each of the remaining sample wells on the sample plate, interpolating intensity data from the intensity data collected for the first set of selected sample wells, forming a two dimensional array from the interpolated intensity values and unfolding the two-dimensional array into a one dimensional column array;

forming a two-dimensional array from the column arrays for each sample well;

inverting the two-dimensional array;

unfolding the image data to form a one dimensional matrix; and multiplying the unfolded image data by the inverted two-dimensional array.

28. The method of claim 27, wherein the sample tray comprises 384 sample wells arranged in 16 rows and 24 columns, the method further comprising collecting intensity data for the 96 sample wells in rows 1, 3, 5, 7, 10, 12, 14, 16 and in columns 1, 3, 5, 7, 9, 11, 14, 16, 18, 20, 22, 24 and interpolating the intensity data for the remaining wells.

29. The method of claim 20, wherein the plurality of luminescent samples each comprise more than one luminescent reagent, each reagent adapted to emit luminescent emissions over a different wavelength spectrum, the method further comprising, for each reagent:

collecting image data using an optical bandpass filter, wherein the optical bandpass filter is adapted to maximize the sensitivity of the charge coupled device to emissions from the reagent; and determining the contribution to the image data of the luminescent emissions from each of the reagents.

30. The method of claim 29, wherein the step of determining the contribution of the luminescent emissions from each of the reagents comprises:

a) for each combination of luminescent reagent and optical bandpass filter, filling each sample well on a sample plate with a sample comprising the luminescent reagent as the sole luminescent reagent, imaging the sample plate using the optical bandpass filter and the total emission filter as a reference, and collecting the image data;

b) normalizing the bandpass filter intensity by the total emission filter intensity;

c) generating a set of simultaneous equations for the image data for the multi-reagent samples as measured through each filter as a function of the contribution to the image data of each of the individual reagents, wherein the image data collected in (a) and normalized in (b) for each combination of luminescent reagent and filter form the respective coefficients for the contribution of each of the luminescent reagents; and c) solving the set of simultaneous equations for the contribution of each of the reagents.

* * * * *